US010900966B2

(12) United States Patent
Liu et al.

(10) Patent No.: US 10,900,966 B2
(45) Date of Patent: Jan. 26, 2021

(54) USE OF GLYCAN AS BIOMARKERS FOR AUTOIMMUNE DISEASES

(71) Applicant: Macau University of Science and Technology, Macau (CN)

(72) Inventors: Liang Liu, Macau (CN); Jing-Rong Wang, Macau (CN); Weina Gao, Macau (CN); Leefong Yau, Macau (CN); Hao Huang, Macau (CN); Qiong Meng, Macau (CN); Tiantian Tong, Macau (CN); Zhi-Hong Jiang, Macau (CN)

(73) Assignee: MACAU UNIVERSITY OF SCIENCE AND TECHNOLOGY, Macau (CN)

( * ) Notice: Subject to any disclaimer, the term of this patent is extended or adjusted under 35 U.S.C. 154(b) by 101 days.

(21) Appl. No.: 16/281,122

(22) Filed: Feb. 21, 2019

(65) Prior Publication Data

US 2019/0178885 A1    Jun. 13, 2019

Related U.S. Application Data

(62) Division of application No. 14/883,622, filed on Oct. 15, 2015, now Pat. No. 10,234,454.

(60) Provisional application No. 62/198,149, filed on Jul. 29, 2015.

(51) Int. Cl.
| | |
|---|---|
| *G01N 33/564* | (2006.01) |
| *G01N 33/48* | (2006.01) |
| *G01N 1/40* | (2006.01) |
| *G01N 30/08* | (2006.01) |
| *G01N 30/60* | (2006.01) |
| *B01L 3/00* | (2006.01) |
| *G01N 30/72* | (2006.01) |
| *G01N 30/88* | (2006.01) |

(52) U.S. Cl.
CPC ...... *G01N 33/564* (2013.01); *B01L 3/502715* (2013.01); *B01L 3/502753* (2013.01); *G01N 1/40* (2013.01); *G01N 30/08* (2013.01); *G01N 30/6095* (2013.01); *G01N 30/7266* (2013.01); *B01L 2200/10* (2013.01); *B01L 2300/069* (2013.01); *G01N 1/405* (2013.01); *G01N 33/48* (2013.01); *G01N 2030/085* (2013.01); *G01N 2030/8836* (2013.01); *G01N 2400/10* (2013.01); *G01N 2440/38* (2013.01); *G01N 2800/102* (2013.01); *Y10T 436/2575* (2015.01)

(58) Field of Classification Search
CPC .......... B01L 2200/10; B01L 2300/069; B01L 3/502715; B01L 3/502753; G01N 1/40; G01N 1/405; G01N 2030/085; G01N 2030/8836; G01N 2400/10; G01N 2440/38; G01N 30/08; G01N 30/6095; G01N 30/7266; G01N 33/48; G01N 33/564; Y10T 436/25; Y10T 436/255; Y10T 436/2575

USPC ....... 436/86, 87, 63, 94, 173, 161, 174, 178, 436/180; 422/70, 502, 503, 527

See application file for complete search history.

(56) References Cited

U.S. PATENT DOCUMENTS

| | | | | |
|---|---|---|---|---|
| 2010/0151584 | A1* | 6/2010 | Parsons | G01N 33/6854 436/94 |
| 2010/0190146 | A1* | 7/2010 | Bynum | G01N 27/44791 435/4 |
| 2014/0030732 | A1* | 1/2014 | Staples | G01N 1/405 435/7.4 |
| 2014/0038215 | A1* | 2/2014 | Smart | G01N 30/6095 435/18 |

OTHER PUBLICATIONS

Chu et al. Proteomics, vol. 9, 2009, pp. 1939-1951.*
Mohammed et al. Journal of Proteome Research, vol. 7, 2008, pp. 1565-1571.*
Zhang et al. Journal of Separation Science, vol. 34, 2011, pp. 2745-2750.*
Jing-Rong Wang, et al. (2017). A method to identify trace sulfated IgG N-glycans as biomarkers for rheumatoid arthritis. Nature Communications doi:10.1038/s41467-017-00662-w.
Jing-Rong Wang, et al.(2018). Reply to 'Trace N-glycans including sulphated species may originate from various plasma glycoproteins and not necessarily IgG'. Nature Communications doi:10.1038/s41467-018-05082-y.
Emanual Maverakis et al. (2015). Glycans in the Immune system and the Altered Glycan Theory of Autoimmunity: A Critical Review. J Autoimmun doi:10.1016/j.jaut.2014.12.002.
Robert M. Anthony et al. (2008). A Recombinant IgG Fc That Recapitulates the Anti-inflammatory Activity of Ivig. Science: 320(5874): 373-376.
Eden P. Go et al.(2011) Characterization of Glycosylation Profiles of HIV-1 Transmitted/Founder Envelopes by Mass Spectrometry. Journal of Virology: p. 8270-8284.

* cited by examiner

*Primary Examiner* — Maureen Wallenhorst
(74) *Attorney, Agent, or Firm* — Eagle IP Limited; Jacqueline C. Lui

(57) ABSTRACT

The present invention discloses a method of determining the presence of autoimmune disease with the use of glycan biomarkers. A method of improving the detection sensitivity of trace glycans from a mixture of glycans and a microfluidic chip therefor are also disclosed.

13 Claims, 22 Drawing Sheets
(22 of 22 Drawing Sheet(s) Filed in Color)

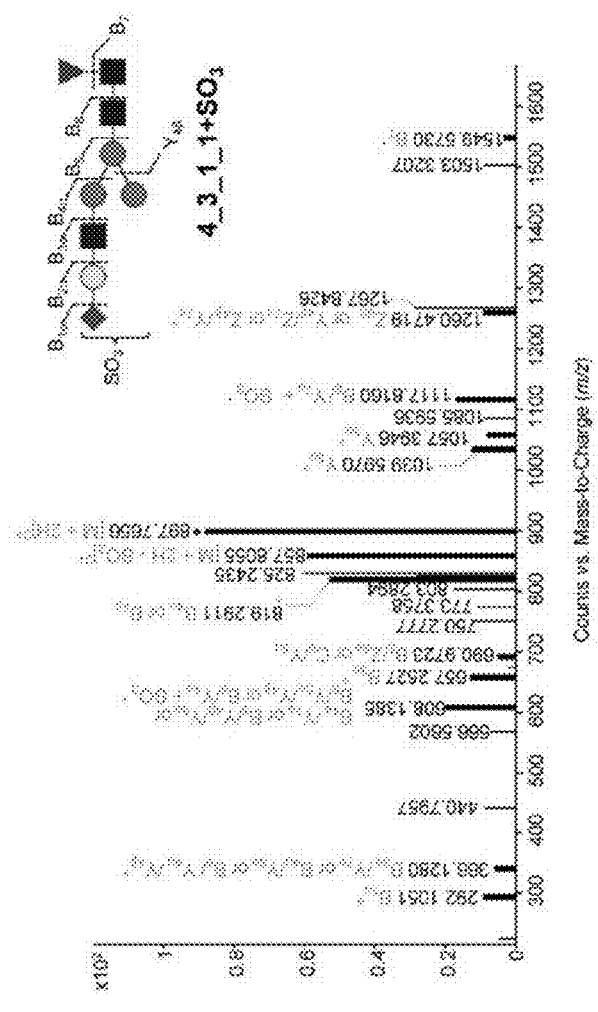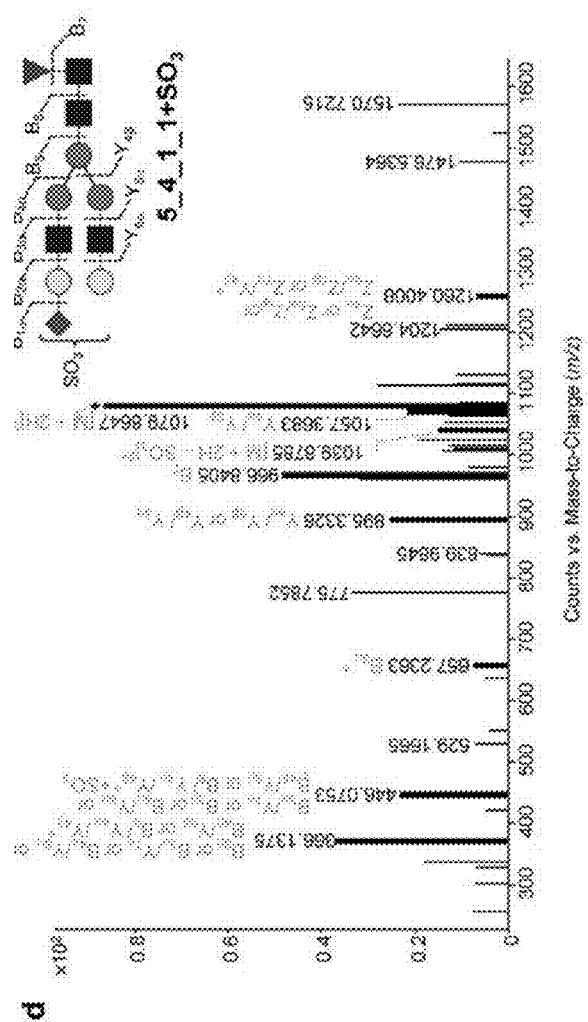

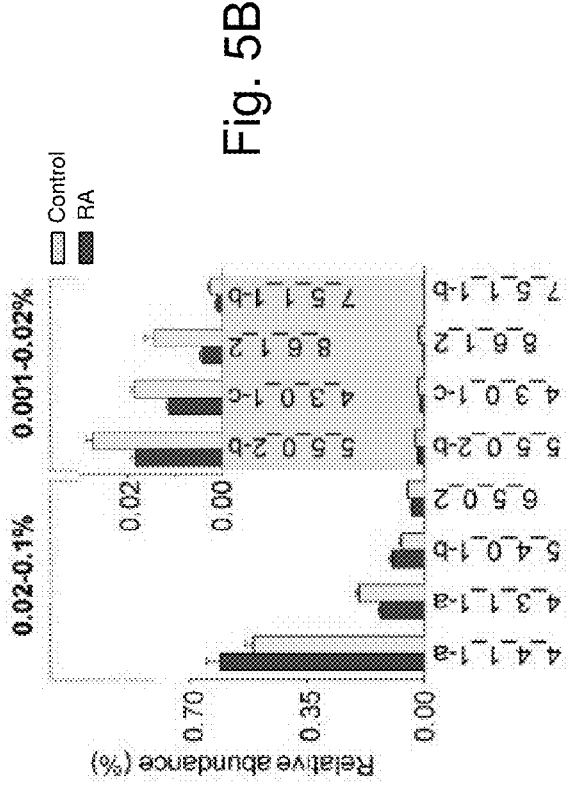
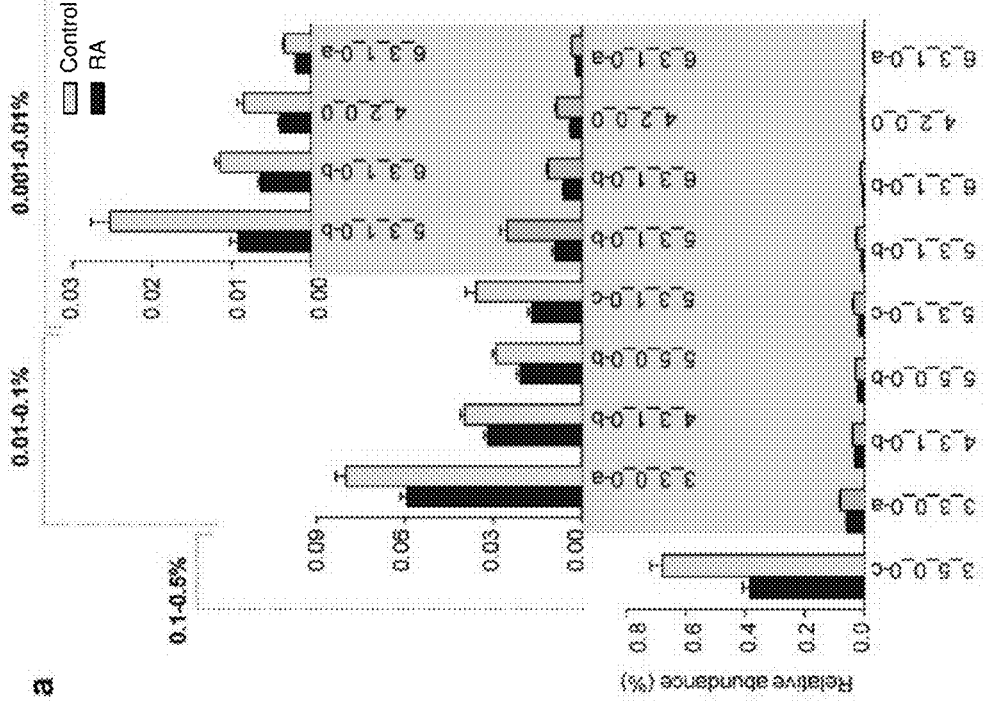
Fig. 5A  Fig. 5B  Fig. 5C

USE OF GLYCAN AS BIOMARKERS FOR AUTOIMMUNE DISEASES

CROSS-REFERENCE TO RELATED APPLICATION

This application claims the benefit under 35 U.S.C. 120 of U.S. patent application Ser. No. 14/833,622, filed Oct. 15, 2015 and now U.S. Pat. No. 10,234,454, which claims benefit under 35 U.S.C. 119(e) of U.S. Provisional Application Ser. No. 62/198,149, filed Jul. 29, 2015, all of which are hereby incorporated by reference herein in their entirety.

FIELD OF INVENTION

This invention relates to and the use of glycans as biomarker for autoimmune diseases.

BACKGROUND OF INVENTION

Glycans are often functional determinants of biological events of immunoglobulin G (IgG), as IgG recognizes and clears pathogens and toxins through coupling specificity of variable region to Fc-mediated cellular functions that are regulated by modulating the composition of the Fc-linked glycans (Maverakis E, et al (2015) J Autoimmun 57 (6): 1-13.). In particular, close association between variations in the glycosylation of IgG and changes in the immune status of humans have long been appreciated, facilitating glycoforms of IgG as molecular signatures for the diagnosis of various diseases like rheumatoid arthritis (RA) and prediction of immune responses. According to Gao et al. (Characterization of glycosylation profiles of HIV-1 transmitted/founder envelopes by mass spectrometry. J Virol. 2011; 85(16):8270-84.), "because of the complexity of samples, wide dynamic range of glycopeptide concentrations, and glycosylation heterogeneity, it is a great challenge to successfully complete glycosylation analysis." Yet, many trace N-glycans are biologically important, e.g., acidic N-glycans with anionic residues, such as sialic acid, sulfate, and phosphate groups. For example, IgGs with sialic acid-terminated N-glycans exhibit anti-inflammatory activities (Anthony R M, et al (2008) Science 320 (5874):373-6). Sulfated glycoproteins are important for biomarker discovery, as well as investigating molecular recognition processes. Therefore, a comprehensive glycomic approach that accounts for low-abundance and difficult-to-detect, but biologically important, species is highly desired.

SUMMARY OF INVENTION

In the light of the foregoing background, it is an object of the present invention to provide an alternate method of improving the detection sensitivity of trace glycan from a mixture of glycans including the steps of:

(a) loading a sample of the mixture of glycans onto enrichment column which is made up of two porous graphitized carbon (PGC) sections and one titanium dioxide ($TiO_2$) section;

(b) running the neutral glycans from step (a) onto an analytical PGC column while acidic glycans are retained on the enrichment column; and (c) running the acidic glycans from step (b) onto the analytical PGC column to achieve analysis of the enriched acidic glycans;

Wherein the enrichment column enriches acidic glycans while analytical PGC column performs chromatographic separation of glycans.

In an exemplary embodiment, the enrichment column includes two porous graphitized carbon sections and one titanium dioxide section, in which the titanium dioxide section is sandwiched between the two porous graphitized carbon sections.

In yet another exemplary embodiment, the trace glycan is acidic glycan; in another exemplary embodiment, the acidic glycan is sulfated glycan. In another exemplary embodiment, the sulfated glycan includes structure set forth in FIG. 3A.

Accordingly, the present invention, in one aspect, is a microfluidic chip for enriching trace glycan from a mixture of glycans having an enrichment column attaching to an analytical column, in which the enrichment column further includes a first section having porous graphitized carbon;

a second section connecting to the first section and having titanium dioxide;

and a third section connecting to the second section and having porous graphitized carbon;

Wherein the analytical column includes porous graphitized carbon and performs chromatographic separation of glycans. The first section and the third section perform pre-enrichment of glycans (including both neutral and acidic glycans) to remove non-glycan constituents. The second section ($TiO_2$) enriches acidic glycans, such that detection sensitivity of low-abundance trace glycans and glycoproteins is highly improved with the use of the microfluidic chip.

According to another aspect of the present invention, a method of determining the presence of autoimmune disease is provided that includes the steps of:

(a) generating a N-glycome of serum IgG of a subject;

(b) identifying a glycan biomarker(s) from the N-glycome;

(c) quantifying relative abundance of the glycan biomarker(s); and (d) determining the presence of the autoimmune disease when relative abundance of the glycan marker(s) exceeds a predetermined threshold value.

In one exemplary embodiment, the autoimmune disease is rheumatoid arthritis. In another exemplary embodiment, the glycan biomarker is sulfated glycan. In yet another exemplary embodiment, the sulfated glycan has a structure set forth in FIG. 3A, item 10 or in FIG. 3A, item 12.

In one exemplary embodiment, the threshold value is 80%.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 2A, FIG. 2B, FIG. 2C, FIG. 2D, FIG. 2E, FIG. 2F and FIG. 2G show the comprehensive profiling of N-glycans on serum IgG.

FIG. 5A, FIG. 5B, FIG. 5C, FIG. 5D, FIG. 5E, FIG. 5F, FIG. 5G, FIG. 5H, FIG. 5I, FIG. 5J, FIG. 5K, FIG. 5L, FIG. 5M and FIG. 5N show the glycan biomarkers of RA.

DETAILED DESCRIPTION OF THE PREFERRED EMBODIMENTS

Figures 1A, 1B, 1C:
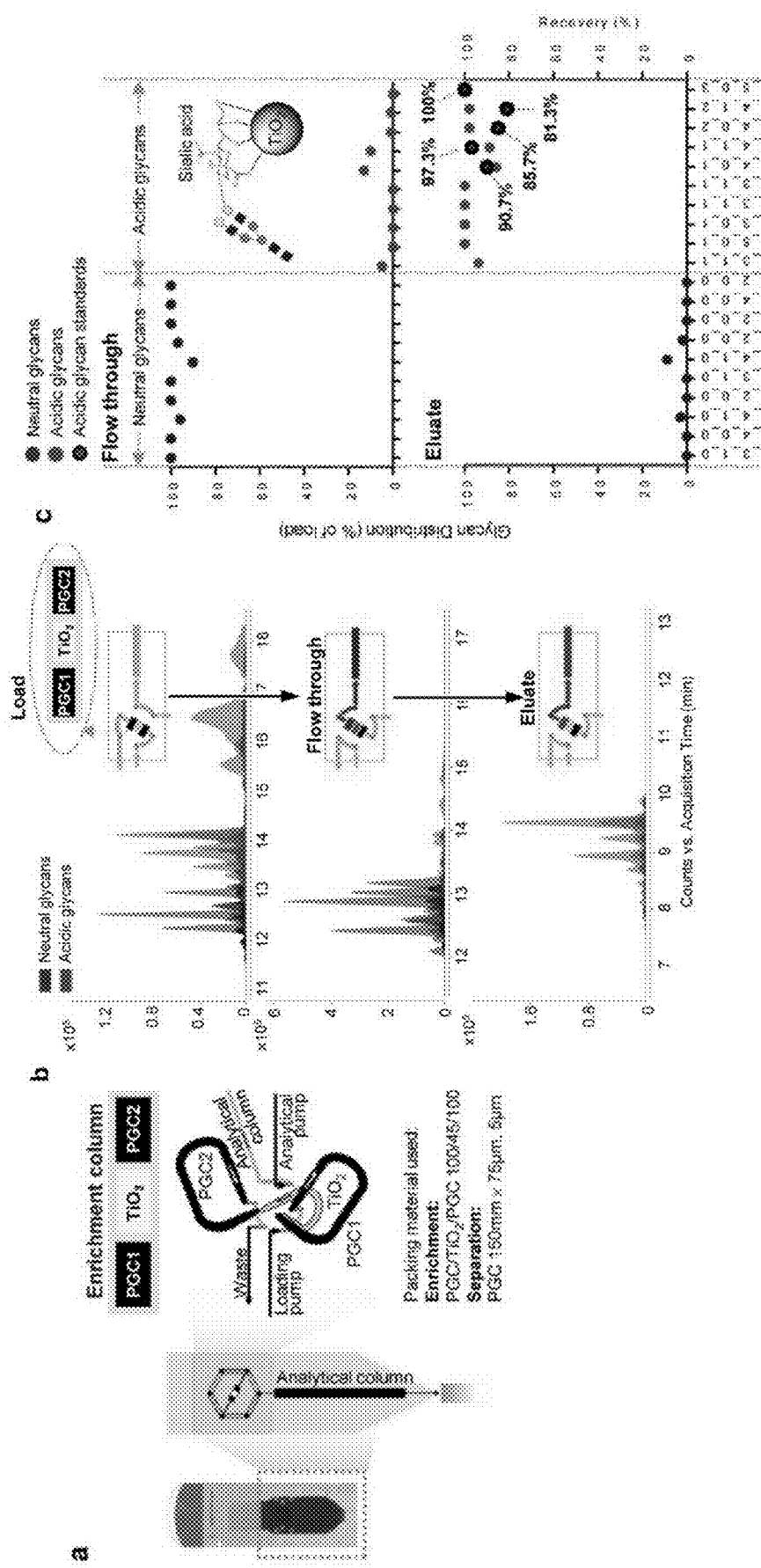
FIG. 1A, FIG. 1B, FIG. 1C, FIG. 1D, FIG. 1E and FIG. 1F illustrate on-chip enrichment of acidic glycans according to one embodiment of this invention.

As used herein and in the claims, "comprising" means including the following elements but not excluding others.

Symbols used in the glycan structure throughout this specification are referenced from "Symbol and Text Nomenclature for Representation of Glycan Structure" from the Nomenclature Committee Consortium for Functional Glycomics accessed on internet on May 2, 2012 at http://www.functionalglycomics.org/static/consortium/Nomenclature.shtml.

The alphabets at the end of the name of a glycan throughout this specification represent the isomers of the glycan with same monosaccharide composition according to their retention time. For example, 4_3_1_1+$SO_3$-b is an isomer of the sulfated glycan 4_3_1_1+$SO_3$ (i.e. item 10 of FIG. 3A).

Generally, different isomers of a glycan with the same monosaccharide composition possess the same properties, but may exhibit quite different functions and effects.

Biological functions of some N-glycans on immunoglobulins (IgGs) are associated with pathogenesis and their therapeutic actions; therefore, the identification of functional N-linked glycans has become a promising area in biomedicine. However, certain low-abundance or trace, but pivotal, species, such as acidic glycans with anionic residues on IgGs, are difficult to detect. Although mass spectrometers with enhanced sensitivity are emerging, the overall increased signal intensity may lead to elevated ion-suppression/interference arising from high-abundance of neutral glycans/matrix at the same time. Enrichment of trace glycans can solve this problem, but it has never been realized on a micro scale.

In this invention, the inventors report a specialized microfluidic chip which integrates a unique enrichment $TiO_2$ column, together with a unique dual-mobile phase approach, allowing the identification of many N-linked glycans on human serum IgGs. Of note, modified glycans, including 20 sulfated and 4 acetylated N-linked glycan compositions, were discovered on IgGs for the first time. Furthermore, by adopting dynamic MRM technique, the inventors have improved the detection sensitivity of acidic glycans by near to a 1000-fold, in turn allowing the precise quantification of many previously undetected low-abundance, trace and even ultra-trace glycans. Thus, for the first time, glycomic profiling was achieved on a "broad" (in number) and "deep" (in sensitivity) level.

Specifically, within the obtained glycan profile of human serum IgGs, the inventors were able to identify trace glycans as biomarkers for autoimmune diseases. Notably, they showed high capacity for accurate classification of rheumatoid factor (RF)-negative rheumatoid arthritis patients, thus showing the potential of these trace and novel glycans as complementary diagnostic indicators of RF. This novel approach could easily reveal potential N-glycosylation-associated biomarkers for other autoimmune and infectious diseases, inspiring the exploration of promising glycoforms of therapeutic antibodies.

1. Methods and Materials 1.1 Collection of Serum Samples.

Serum samples of Rheumatoid Arthritis (RA) patients (n=90) and healthy subjects (n=57) were collected from the Division of Rheumatology of Jiujiang No. 1 People's Hospital (Jiujiang City, China). This study was approved by the Ethics Committee of Jiujiang No. 1 People's Hospital. The methods were carried out in accordance with the approved guidelines. All serum samples were stored at −80° C. prior to analysis.

1.2 Materials and Reagents.

All glycan standards, including neutral N-glycans, acidic N-glycans ($Hex_5HexNAc_4NeuAc_1$, $Hex_5HexNAc_4NeuAc_2$, $Hex_5HexNAc_4dHex_1NeuAc_1$, $Hex_5HexNAc_4dHex_1NeuAc_2$, and $Hex_6HexNAc_5NeuAc_3$), high mannose N-glycans ($Hex_5HexNAc_2$, $Hex_6HexNAc_2$, $Hex_7HexNAc_2$, and $Hex_8HexNAc_2$), and an acidic O-glycan (LSTc) were purchased from Prozyme (Hayward, Calif., USA). rProtein A Sepharose™ 4 Fast Flow (90 μm) was obtained from GE Healthcare (Uppsala, Sweden). PNGase F (500,000 units/ml) was a product of New England Biolabs, Inc. (Beverly, Mass., USA). Dye reagent concentrate for protein assay was purchased from Bio-Rad (Hercules, Calif., USA). Recombinant human N-acetylglucosamine-6-sulfatase (NG6S) was purchased from Novoprotein, and galactose-6-sulfatase (GALNS) was purchased from Abnova. Sialidase C was a product of Glyko Biomedical Ltd., and other exoglycosidases, including β1-4 galactosidase, β-N-acetyl glucosaminidase and α1-2,3 mannosidase, were purchased from New England Biolabs Inc. Multiscreen Solvinert Filter plates (96 wells, 0.45 μm, hydrophilic PTFE) and Amicon Ultra-0.5 100K centrifuge filter devices were purchased from Millipore (Merck Millipore, County Cork, Ireland). V-bottom 96-well collection plates and Sep-Pak $C_{18}$ cartridges were purchased from GE Healthcare and Waters (Milford, Mass., USA), respectively. Strong anion exchange (SAX) Ultra-Micro SpinColumns were purchased from Harvard Apparatus (Holliston, Mass., USA), and HyperSep Hypercrab porous graphitic carbon (PGC) cartridges were purchased from Thermo Fisher Scientific (Pittsburgh, Pa., USA). Acetonitrile and methanol (both LC-MS grade) were purchased from Avantor (Center Valley, Pa., USA), while LC-MS grade formic acid, acetic acid and ammonia solution were purchased from Sigma-Aldrich (St. Louis, Mo., USA). All other chemicals were of analytical reagent grade. Distilled water was prepared by using Milli-Q system (Millipore Ltd., Watford, UK).

1.3 Preparation of Standard Solutions.

Glycan standards were individually reconstituted in distilled water to yield stock solutions at a concentration of 100 μg/mL. The resulting individual stock solutions were then mixed and diluted to afford a series of working solutions (0.003-400 nM) for standard curve construction and assessment of sensitivity and repeatability. Five acidic glycan standards were mixed to prepare an additional stock solution of mixed acidic glycan standards which was further diluted to 2 different concentrations (1.56 nM and 12.5 nM) for evaluating on-chip enrichment recovery rate. For binding capacity assessment, each acidic glycan was diluted individually to the concentrations ranging from 10 to 5120 nM. All stock solutions were stored at −20° C. before use, and all working solutions were freshly prepared.

1.4 Capture of IgGs from Serum Samples.

rProtein A Sepharose™ 4 Fast Flow beads were applied to a 96-well filter plate at 50 μL per well. After washing twice with 5 volumes of binding buffer (20 mM sodium phosphate, pH 7.0), 250 μL binding buffer and 10 μL serum were successively applied into each well. The plate was sealed and incubated on a shaker at room temperature for 15 min.

The filtrate was collected in a V-bottom collection plate by centrifugation (1000 rpm, 5 min). The retained beads were washed twice with 250 µL binding buffer. IgGs (IgG1, IgG2 and IgG4) were then eluted twice with 200 µL elution buffer (0.1 M glycine buffer, pH 2.7) into a new V-bottom collection plate. 30 µL neutralizing buffer (1 M Tris-HCl, pH 9.0) was subsequently added for neutralization. The obtained IgG samples were then transferred to 100K centrifuge filter units for exchanging buffer, and the resulting water solution was concentrated to a final volume of 30 µL. The amount of captured IgGs in each sample was quantitated by using Bio-Rad protein assay. The purity of captured IgGs was examined by using SDS-PAGE and HPLC.

1.5 Release of N-Glycans.

50 µg IgGs of each sample were taken out and diluted with 100 mM ammonium bicarbonate buffer (pH 7.4) to a final concentration of 1 µg/µL. Then 0.5 µl PNGase F was added, followed by 16-hour incubation at 37° C. The cleaved N-glycan was loaded onto a $C_{18}$ cartridge to remove the de-glycosylated protein. The N-glycans sample was directly loaded onto the preconditioned cartridge and washed with 0.5 mL of distilled water. The flow-through and water eluate were combined and dried by speed vacuum. The dried residues were reconstituted in 100 µL distilled water and stored at −80° C. before analysis.

1.6 Offline Enrichment of Acidic N-Glycans by Using Strong Anion Exchange (SAX) Spin-Columns.

SAX spin-columns were preconditioned using 3 bed volumes of 0.05% formic acid (FA) aqueous solution 3 times. The total N-glycans released from serum IgG were suspended in 0.05% FA aqueous solution before passing through the preconditioned SAX spin-column. The spin-columns were then washed twice with 3 bed volumes of 0.05% FA aqueous solution, and the bound acidic glycans were eluted twice using 3 bed volumes of 1M NaCl aqueous solution. The eluate was desalted using a PGC cartridge column and dried by speed vacuum. In the PGC desalting procedure, the column was preconditioned by 5 bed volumes of acetonitrile (ACN) and 0.1% FA aqueous solution, respectively. Sample was loaded by gravity settling and then washed twice with 1 bed volume of 0.1% FA aqueous solution. The bound acidic glycans were eluted twice using 1 bed volume of 80% ACN (pH 7.0, adjusted by 0.5% FA). The unbound neutral glycan fraction was treated as complex neutral glycan mixture for subsequent validation experiments.

1.7 HPLC-Chip/MS Analysis.

An Agilent 1260 Infinity HPLC-Chip LC system (Agilent, Santa Clara, Calif., USA) was coupled to an Agilent 6550 iFunnel Quadrupole Time-of-Flight (Q-TOF) mass spectrometer (MS) for N-glycans profiling or coupled to an Agilent 6490 iFunnel Triple Quadrupole (QqQ) MS for N-glycans quantification. The Agilent 1260 Infinity HPLC-Chip system was equipped with a HiP micro ALS sampler with a 40 µL sample loop, a nanoflow pump, a capillary pump, an HPLC-Chip Cube Interface, a thermostat and a µ-degasser. A 25 µm ID PEEK capillary was used for sample transfer in order to prevent dissolution of fused silica by high-pH elution buffer.

$TiO_2$-PGC Chip.

A customized $TiO_2$-PGC chip is comprised of a 75 µm×150 mm PGC analytical column (PGC 5 µm) and a three-sectioned enrichment column, including a first 100 nL PGC section (PGC 5 µm), a 45 nL $TiO_2$ section, and a second 100 nL PGC section (Agilent, Waldbronn, Germany) The $TiO_2$-PGC chip was operated in forward flush mode. 2 µL of sample were first injected and transferred to the enrichment column using 0.6% acetic acid, 2% FA and 2% ACN in water at a flow rate of 3 µL/min. The chip valve was switched 2 min after injection to place the enrichment column in-line with the analytical column. Mobile phase used in the nanoflow pump was optimized for neutral glycans consisting of 1% FA in water (A) and ACN (B). The gradient was performed at a flow rate of 0.5 µL/min, as follows: 5% B for 6 min, 5-60% B in 10 min, 80% B for 3 min. The acidic glycans were subsequently eluted by injecting 5 µL of elution buffer (0.5% ammonia solution in water). The analysis of the eluted glycans was performed by switching the enrichment column in-line with the analytical column 1 min after injection. The mobile phase optimized for acidic glycans was used. Mobile phase A was 0.5% FA in water and adjusted to pH3 by ammonia solution, while mobile phase B was 1% FA in ACN. The flow rate was 0.5 µL/min, and the gradient was as follows: 5% B for 1 min, 5-60% B in 10 min, 80% B for 3 min. Equilibrium time of 18 min was set before each injection.

PGC Chip.

The PGC chip consisted of a 75 µm×150 mm analytical column and a 75 µm×9 mm enrichment column, both packed with 5 µm PGC as the stationary phase. A flow rate of 3 µL/min of 0.1% FA in water was used for sample loading with 2 µL injection volume. The mobile phase for nanopump contained 0.5% FA in water adjusted to pH3 by ammonia solution (A) and 1% FA in ACN (B) for acidic glycans analysis, while the mobile phase of 1% FA in water (A) and ACN (B) was used for neutral glycans analysis. The flow rate was 0.5 µL/min, and the gradient was as follows: 5% B for 6 min, 5-60% B in 10 min, 80% B for 3 min. Equilibrium time of 18 min was set before each injection.

All profiling and MS/MS analysis were carried out by an Agilent 6550 iFunnel Q-TOF MS. The dry gas ($N_2$) temperature and flow rate were 225° C. and 11 L/min, respectively. MS spectra were acquired in positive mode, and the mass range was m/z 500 to m/z 3000 with an acquisition time of 1 spectrum/s. Mass correction was enabled using reference masses of m/z 922.0098 and m/z 1221.9906. The mass range of MS/MS experiments was m/z 100 to m/z 3000. Spectra were acquired in targeted MS/MS mode with MS acquisition rate of 2 spectra/s and MS/MS acquisition rate of 3 spectra/s. The collision energy (CE) was set at 10-40 eV. Quantitation was performed with an Agilent 6490 iFunnel Triple Quadrupole (QqQ) MS. The MS was operated in positive mode. The dry gas ($N_2$) temperature and flow rate were 225° C. and 11 L/min, respectively. RF voltage amplitude of high pressure and low pressure ion funnel were 150 V and 200 V, respectively. The dynamic MRM mode was used, and the cycle time was fixed at 500 ms. All data was processed using Agilent MassHunter Qualitative Analysis B.06.00 software and Agilent MassHunter Quantitative Analysis B.06.00 software.

1.8 Binding Capacity of Acidic N-Glycans on $TiO_2$-PGC Chip.

The binding capacity of acidic glycans on $TiO_2$-PGC chip was evaluated by employing a breakthrough experiment. The serial concentrations of individual acidic glycan standards were loaded onto the enrichment column of $TiO_2$-PGC chip successively with elution steps after each loading. The amount of the acidic glycan eluted in the loading and elution steps was determined by on-line detection. The overloaded fraction was collected from the waste tube and concentrated for analysis. The breakthrough percentage was calculated by using the following formula: (signal in loading step+signal in overloaded fraction)/total signal×100%. The breakthrough curve was constructed by the percentage of breakthrough against glycan concentration, and the binding capacity was estimated as the amount of binding that occurred before the breakthrough percentage reached 10% ($QB_{10}$).

1.9 Comparison of the Enrichment Performance of $TiO_2$-PGC Chip and Offline SAX for Acidic Glycans.

Total N-glycans of serum IgG were analyzed by $TiO_2$-PGC chip coupled to Q-TOF MS as described above, while the bound acidic glycans eluted from SAX spin-columns were analyzed by PGC chip coupled to Q-TOF MS. The number of acidic glycans and the pattern of acidic glycans under both methods were compared in order to evaluate their enrichment performance for acidic glycans. Meanwhile, 6 replicates of analysis under both methods were carried out for the assessment of the reproducibility of $TiO_2$-PGC chip and offline SAX in terms of RSD %.

1.10 Identification of Sulfation Sites by Using Exoglycosidases.

Four exoglycosidases, including sialidase C, β1-4 galactosidase, β-N-acetyl glucosaminidase, and α1-2,3 mannosidase, were employed to hydrolyze the glycans, respectively, to determine the monosaccharide linked with the sulfate group.

Sialic acids were released by enzymatic digestion using sialidase C. Briefly, 20 µg IgG glycan were reconstituted with 100 µL of 50 mM $NH_4Ac$ (pH 5.0), and 5 µL of sialidase C (0.05 units) were added subsequently. The solution was incubated at 37° C. for 18 h, and the digestion was then terminated by heating the solution in boiling water for 5 min. The digestion was evaporated by speed vacuum and then redissolved in 40 µL $H_2O$. After centrifugation at 14000 g for 15 min, 30 µL of the supernatants were loaded into the vial insert with 1 µL of the acidic glycan IS. For blank samples, 5 µL of $H_2O$, instead of sialidase C, were added.

β1-4 galactosidase was employed to digest the β1-4 linked galactose. 20 µg IgG glycan and 1 µL of β1-4 galactosidase (8 units) were incubated in sodium citrate (50 mM, pH 6.0) and NaCl (100 mM) reaction buffer for 1 h at 37° C. in a total reaction volume of 10 µL. After dilution to 40 µL, the solution was centrifuged at 14000 g for 15 min, and 30 µL of the supernatants were loaded into the vial insert with 1 µL of the acidic glycan IS. For blank samples, 1 µL of $H_2O$ took the place of β1-4 galactosidase.

β-N-acetyl glucosaminidase was used to cleave the β-N-acetyl glucosamine residues from oligosaccharides. Briefly, 20 µg IgG glycan and 1 µL of β-N-acetyl glucosaminidase (4 units) were incubated in sodium citrate BSA buffer (50 mM, pH 6.0) for 4 h at 37° C. in a total volume of 10 µL. After dilution to 40 µL, the solution was centrifuged at 14000 g for 15 min, and 30 µL of the supernatants were loaded into the vial insert with 1 µL of the acidic glycan IS. For blank samples, 1 µL of $H_2O$ took the place of β-N-acetyl glucosaminidase.

α1-2,3 mannosidase was employed to digest the α1-2,3 mannose residues from oligosaccharides. 20 µg IgG glycan and 1 µL of α1-2,3 mannosidase (32 units) were incubated in sodium acetate (50 mM, pH 5.5) and $CaCl_2$ (5 mM) BSA buffer for 1 h at 37° C. in a total volume of 10 µL. After dilution to 40 µL, the solution was centrifuged at 14000 g for 15 min, and 30 µL of the supernatants were loaded into the vial insert with 1 µL of the acidic glycan IS. For blank samples, 1 µL of $H_2O$ took the place of α1-2,3 mannosidase.

All samples in the sulfatase and exoglycosidase experiments were prepared in duplicate.

1.11 Method Validation.

Calibration curves. A linear regression equation, y=ax+b, was created to correlate the peak area to the glycan concentration. The linearity was verified by correlation coefficients ($r^2$), and the slope (a) of the standard curve represented the response factors which displayed the MS response of each glycan. The linear range and response factors of each glycan standard measured on QqQ MS in MRM mode and Q-TOF MS were compared.

On-Chip Enrichment Recovery.

Two concentrations of acidic glycan standard mixture (1.56 nM and 12.5 nM) and the same concentration of acidic glycan standard mixture spiked into complex neutral glycan mixture were analyzed by using $TiO_2$-PGC-chip in forward (with enrichment) and backward flush mode (without enrichment), respectively. The signal of each acidic glycan in both flush modes was measured in 6 replicates by using QqQ MS in MRM mode. The recovery rate was calculated by the following formula: signal in forward flush mode/signal in backward flush mode×100%.

Sensitivity.

The limits of quantification (LOQ) were determined on the basis of response at signal-to-noise (S/N) of 10. Using QqQ MS in MRM mode and Q-TOF MS, the sensitivity of each N-glycan standard and an internal acidic glycan standard (LSTc) was compared relative to LOQ. The sensitivity of acidic glycans with and without on-chip enrichment was also compared according to the MRM signal of LSTc which was spiked into complex neutral glycan mixture derived from the total N-glycans of serum IgG.

Repeatability.

Three concentrations of total glycan standard mixture (0.19 nM, 1.56 nM and 12.5 nM) were analyzed by $TiO_2$-PGC-chip using QqQ MS in MRM mode for 6 replicates. The repeatability of $TiO_2$-PGC-chip was compared with PGC-chip in terms of relative standard deviation (RSD %).

2. Discussion of Results

Chromatographic enrichment is essential for improving detection sensitivity of low-abundance acidic glycans and glycoproteins. To automate the process, the inventors designed a special microfluidic chip in which a titanium dioxide ($TiO_2$) column enriches acidic glycans, while a porous graphitized carbon (PGC) column performs chromatographic separation of glycans, resulting in an integrated glycomic approach enabling comprehensive profiling of N-glycans and accurate quantification of extremely low-abundance N-glycans, particularly acidic species.

More specifically, as shown in FIG. 1A that shows the structure of the specialized $TiO_2$-PGC chip, this specialized microfluidic chip contains a "sandwich-like" enrichment column composed of one $TiO_2$ section and two PGC sections (PGC1 and PGC2 in FIG. 1A) to enrich acidic glycans. This "sandwich" design allows the enrichment of glycans on $TiO_2$ after a continuous "pre-fractionation" on PGC (PGC1, FIG. 1A), thus affording the ability to enrich trace species from a complex glycan pool. $TiO_2$ has been shown to have high affinity for negatively charged molecules in phosphorylated or sialylated species. Accordingly, fast and highly selective on-chip enrichment of acidic glycans was achieved on the basis of the high selectivity of $TiO_2$ towards negatively charged glycans. Using a complex mixture obtained from serum IgGs, the inventors demonstrated that low-abundance acidic glycans could be separated from much more abundant neutral glycans with high selectivity (>80%, as shown in FIGS. 1B and 1C) on this specialized chip. This capability coupled with relatively high binding capacity of the enrichment column facilitated a broad and dynamic range of on-chip enrichment, as shown by quantitative enrichment of acidic glycans from total glycans of 0.03-0.5 µg IgG.

In one embodiment, the function of first section (PGC1) is to enrich all glycans by removing other non-glycan substances. The enriched glycans are then brought onto the $TiO_2$ section to enrich acidic glycans because acidic glycans have higher affinity to $TiO_2$. This design ensures that only glycans (without other non-glycan constituents) are enriched by the $TiO_2$ section, thus greatly improving the enrichment efficacy of $TiO_2$. The third section (PGC2) functions in a similar manner as that of first section.

In particular, FIG. 1B shows extracted compound chromatograms (ECC) of N-glycans detected in load, flow-through/wash (neutral glycans) and eluate fractions (acidic glycans) of $TiO_2$ enrichment column as analyzed by liquid chromatography coupled with nanoelectrospray ionization quadrupole time-of-flight mass spectrometry in positive mode. FIG. 1C shows that $TiO_2$ enrichment column selectively captures acidic N-glycans. Neutral N-glycans do not efficiently bind to $TiO_2$ and therefore are recovered in the flow-through and wash fractions, while acidic glycans are retained on $TiO_2$ during load and flow-through steps and are eluted out by plug of elution buffer. Enrichment recovery rates (numbers beside the dot) of five acidic glycan standards (dot with black circle) were also provided.

Figure 1E:
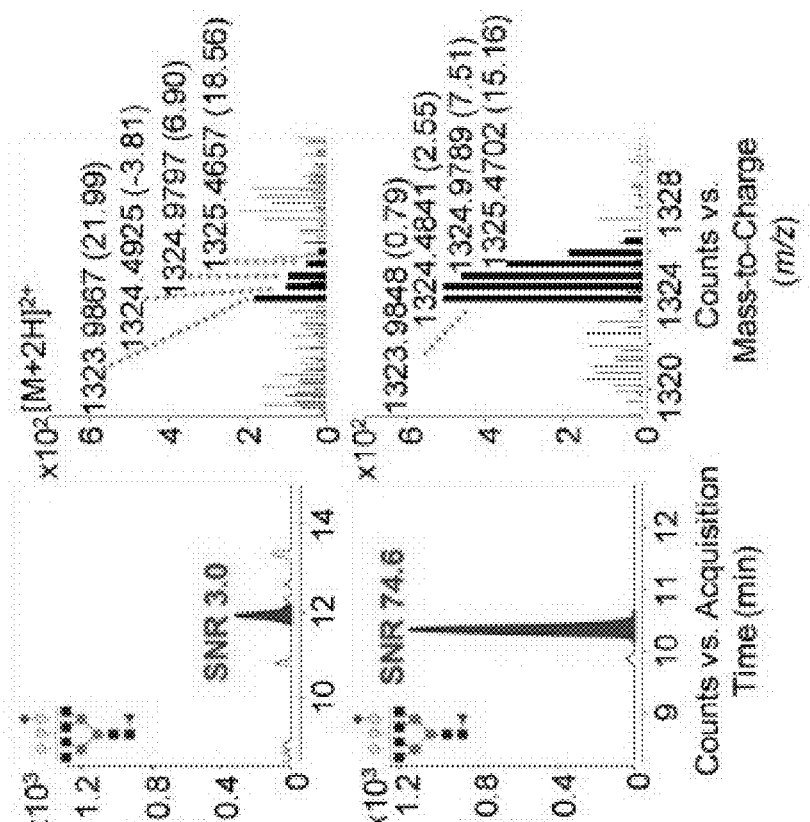
Figure 1D:
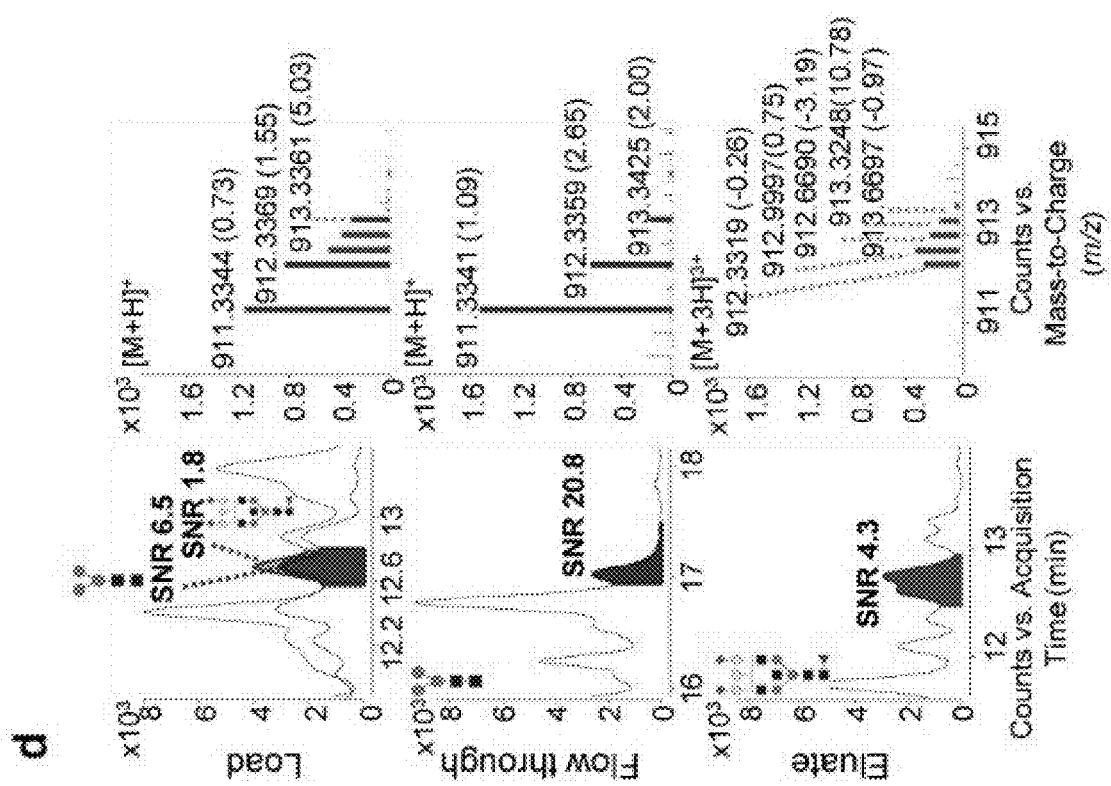
Figure 1F:
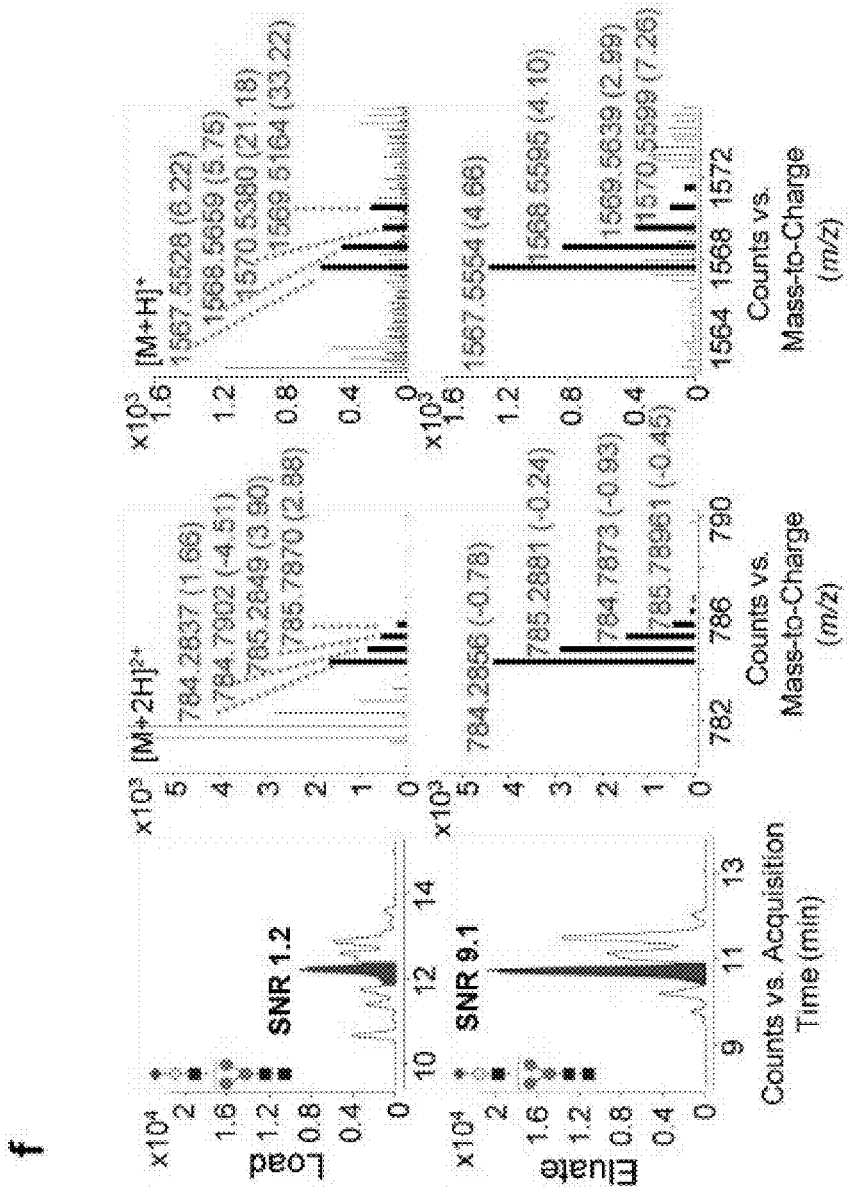

Detection of low-abundance acidic glycans was achieved by (1) improved sensitivity, owing to decreased ionization suppression derived from otherwise co-eluted neutral glycans and/or other matrix components, as evidenced by up to 25-fold increase of S/N ratio of acidic glycans as compared to PGC-chip (as shown in chromatograms of FIGS. 1D-1F); (2) enhanced mass accuracy and isotope distribution of the intact glycan's ion, owing to the removal of neutral glycans and/or other molecules with similar molecular weight (as shown in mass spectrum of FIGS. 1D to 1F); and (3) reliable MS/MS measurement by removing isomeric and/or isobaric ions that could pass through the quadrupole to undergo fragmentation and thereby compromise the fragmentation information. Meanwhile, taking advantage of dual-mode analysis by the $TiO_2$-PGC-chip, the inventors developed a "dual mobile phase" approach which maximized the detection sensitivity of all three types of N-glycans, i.e., high mannose, neutral complex/hybrid, and acidic complex/hybrid N-glycans, respectively, by at least 5-fold over that of the routinely used mobile phase. These concurrent improvements provide a firm basis for the detection of low-abundance acidic glycans, which cannot otherwise be achieved by simple improvement of the overall signal intensity.

In particular, in FIG. 1D, the $[M+3H]^{3+}$ ions of an acidic glycan were overlapped with the isotopic ions of co-eluted neutral glycan and thus could not be assigned. Using $TiO_2$-PGC chip of the instant invention, the acidic glycan was enriched efficiently and, hence, detected with enhanced signal-to-noise ratio (SNR) and improved mass accuracy owing to the removal of interference from neutral glycans; in FIG. 1E, the signal intensity, as well as SNR of an acidic glycan, enhanced significantly after on-chip enrichment owing to the reduced ion-suppression derived from neutral glycans/matrix. In FIG. 1F, with the removal of noise derived from neutral glycans/matrix, mass accuracy of acidic glycan was significantly enhanced, thus providing reliable evidence for the identification of the acidic glycan. The number in bracket beside each mass value indicates the mass error (ppm).

Figure 2A:
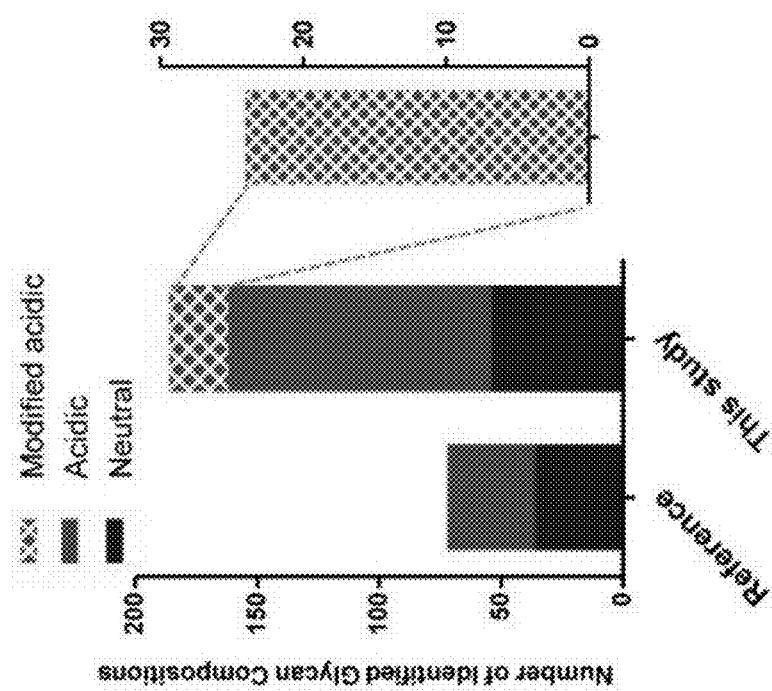

This integrated glycomic approach enabled the most comprehensive profiling of N-glycans on IgGs thus far reported. Using ~2.5 µg serum polyclonal IgGs, a total of 471 glycans arising from 186 distinct compositions were identified in the current study, including 54 compositions of neutral glycans and 132 compositions of acidic glycans. The glycans identified represent 56% coverage of the theoretical N-glycan library for serum developed recently. Of note, identifications from the inventors doubled the number of known neutral N-glycans of IgG (36 compositions) and almost quadrupled the number of acidic N-glycans previously identified on IgG (36 compositions), as shown in FIG. 2A, which shows the number of N-glycans characterized on serum IgGs by using $TiO_2$-PGC-chip of the instant invention coupled with Q-TOF MS. The additionally identified glycans not only demonstrated a sharp increase in the detection capability for acidic N-glycans by the on-chip method, but also suggested a remarkable and unpredicted structural diversity of acidic glycans on IgG.

Figures 2B, 2C:
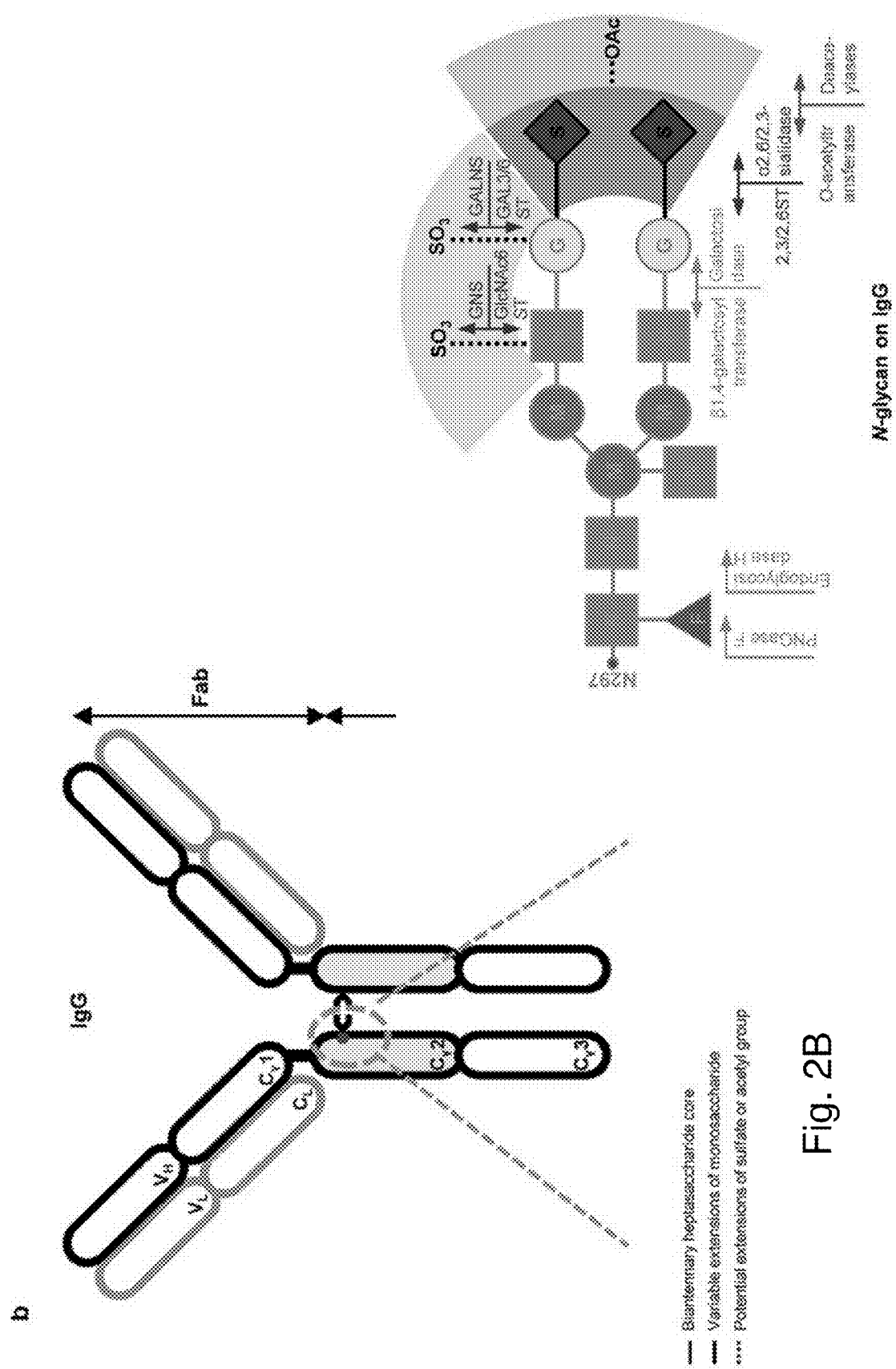
Figure 2F:
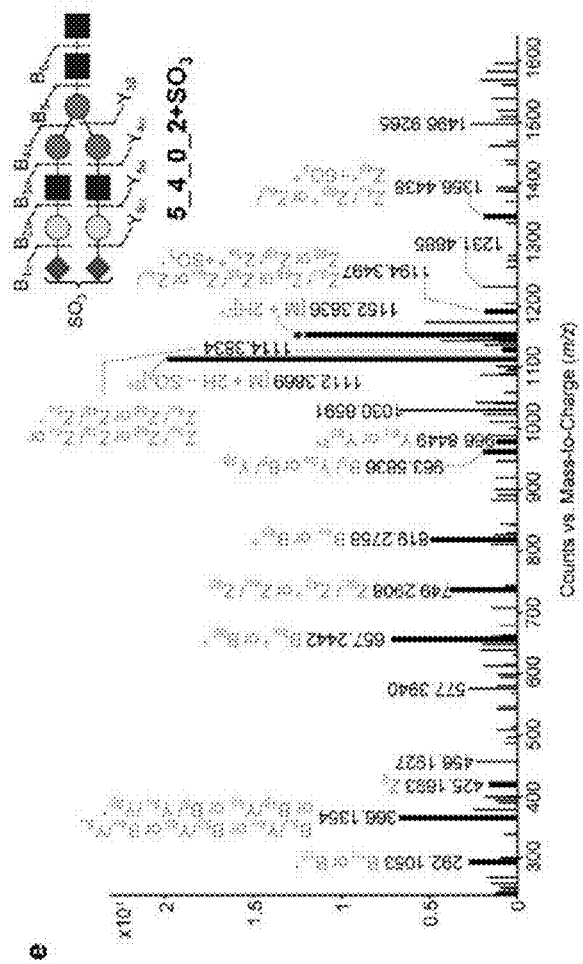
Figure 2G:
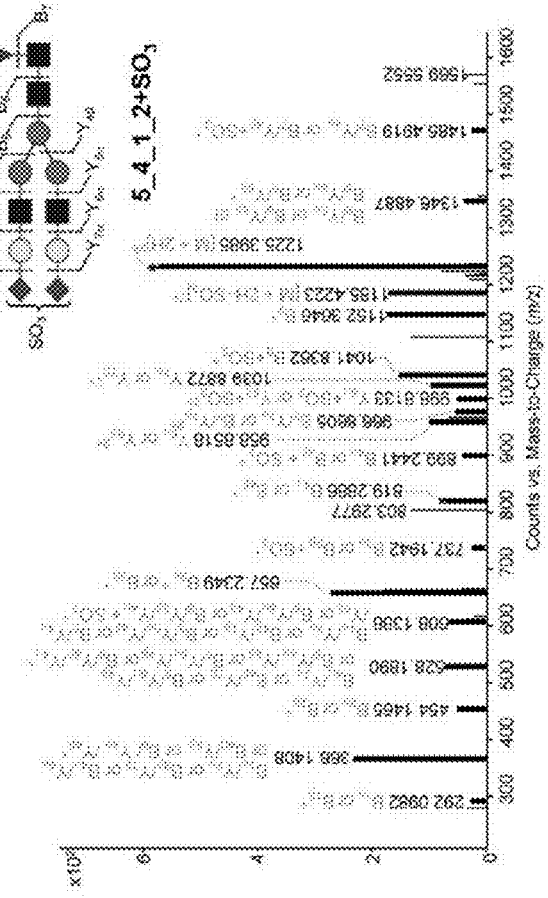

The comprehensive profiling of acidic glycans resulted from an enlarged bioinformatics framework can be attributed to (1) variation in saccharide composition and (2) modification of the core structures. The novel saccharide compositions of acidic N-glycans on IgG were featured by multiple fucoses (2-3) with 0-4 sialic acids attached on tri-, tetra- or penta-antennary core glycan structure, while modification of the core structures includes sulfation and O-acetylation as shown in FIGS. 2B-2C, which are structure maps of N-glycans on IgG.

Figure 3A:
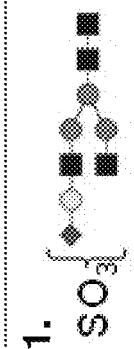
FIG. 3A, FIG. 3B, FIG. 3C, FIG. 3D and FIG. 3E show the structures of sulfated glycans identified on human serum IgGs.

Sulfation has never been observed on serum glycoproteins of human More importantly, many sulfated glycans (33 structures arising from 20 distinct compositions) were discovered, among which 4 compositions have been previously found in human urine, 2 compositions were revealed on porcine thyroglobulin, and 14 compositions, as shown in FIG. 3A, have not been reported before. In particular, FIG. 3A shows the structures of the 20 identified sulfated glycans in human serum IgG (*represents the 4 sulfated glycans reported from human source, but not from IgG; #represents the 2 sulfated glycans reported in porcine thyroglobulin; another 14 sulfated glycans have thus far not been reported).

Figure 3B:
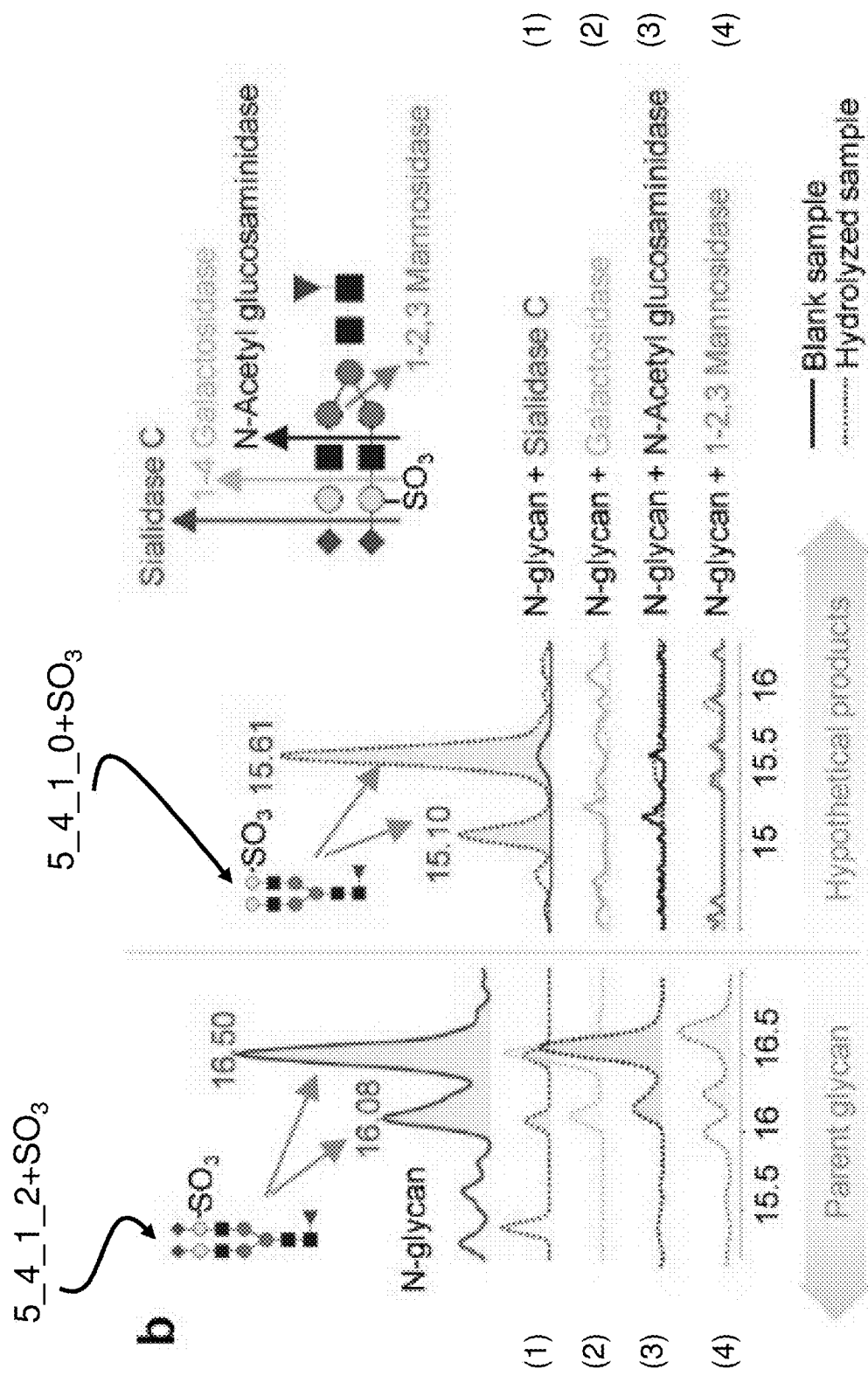
Figure 3C:
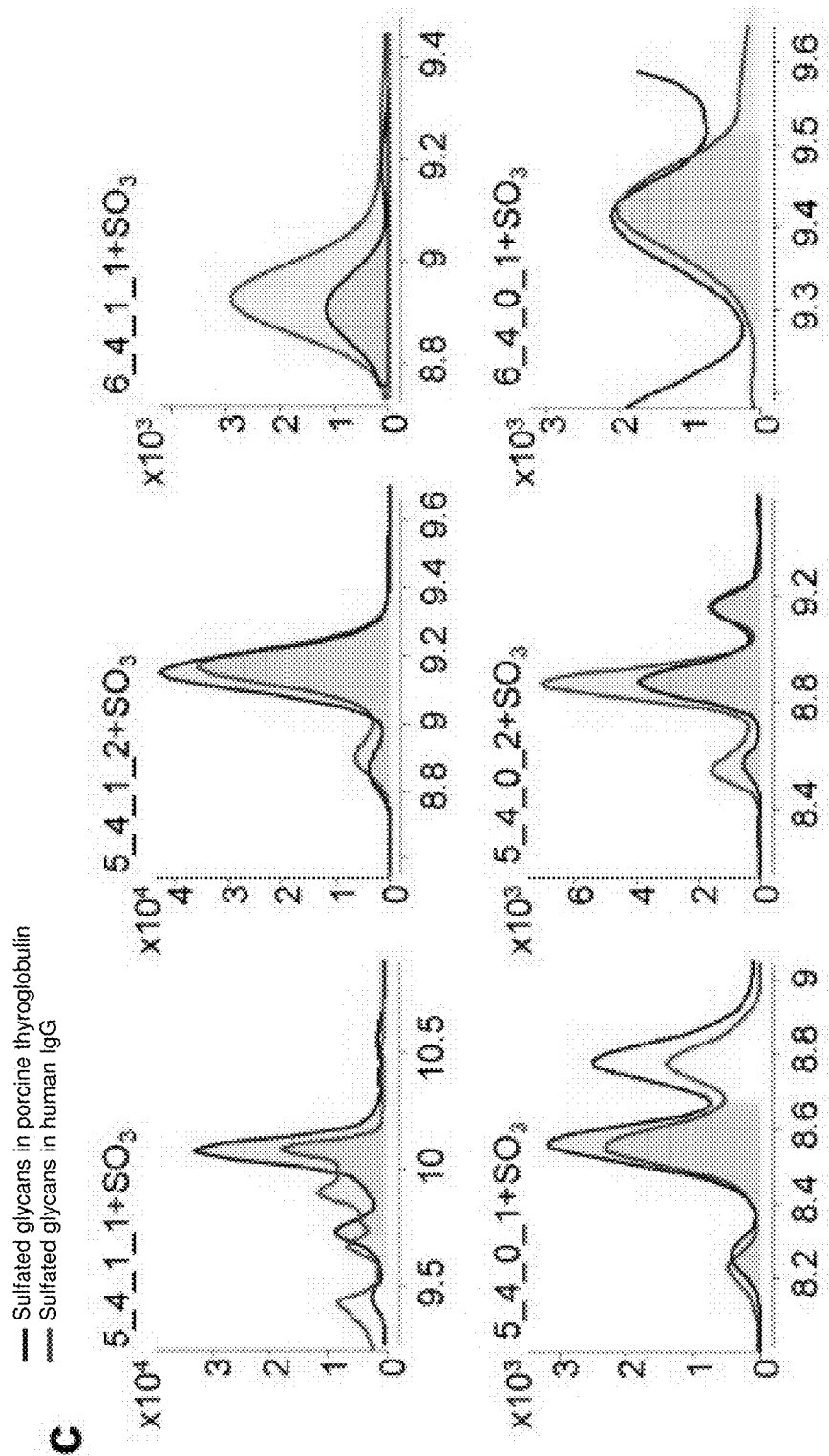

A total of 18 out of the 20 compositions were assigned based on their accurate mass and fragments derived from in-source neutral loss $[M-80]^+$, and 8 compositions were further confirmed by high-resolution MS/MS, in which four typical MS/MS spectrum of sulfated glycans were shown in FIG. 2D-2G as example. The sulfate groups were confirmed by sulfatase assay for 3 compositions, and their locations were further determined by using a series of exoglycosidases compared with those of well-characterized sulfated glycans obtained from porcine thyroglobulin (as shown in FIGS. 3B and 3C). FIG. 3B shows that four exoglycosidases, including sialidase C, β1-4 galactosidase, β-N-acetyl glucosaminidase, and α1-2,3 mannosidase, were employed to hydrolyze the corresponding glycans, respectively, in order to determine the monosaccharides that were linked to the sulfated groups. Taking sulfated N-glycan 5_4_1_2+$SO_3$ (i.e. item 13 of FIG. 3A) as example, two peaks corresponding to 5_4_1_2+$SO_3$ were clearly observed in the extracted compound chromatogram of blank sample (the top peak of the plot for the parent glycan), indicating two isomers of this sulfated N-glycan. After incubation with sialidase C (dotted chromatogram, curve (1)), 5_4_1_2+$SO_3$ decreased concomitantly with significant increase of 5_4_1_0+$SO_3$, which can hardly be detected in blank sample. The peak intensities of 5_4_1_2+$SO_3$ decreased in galactosidase/N-Acetyl Glucosaminidase/1-2,3 Mannosidase-hydrolyzed samples (as shown in curves (2), (3) and (4) respectively), but the hypothetical products 3_4_1_0+$SO_3$/3_2_1_0+$SO_3$/3_3_1_1+$SO_3$ could not be found in either blank or hydrolyzed samples. The results gave evidence that the sulfated group may not be linked to the 3_4_1_0/3_2_1_0/3_3_1_1 residue of 5412+SO$_3$. The sulfation sites of two other sulfated N-glycans, including 5_4_1_1+SO$_3$ (i.e. item 12 of FIG. 3A) and 5_4_0_2+SO$_3$ (i.e. item 3 of FIG. 3A), were confirmed by using this method. FIG. 3C shows the retention time and peak patterns of sulfated N-glycans in human IgG (red) were compared with those in porcine thyroglobulin (blue), which has been well characterized.

Figure 3D:
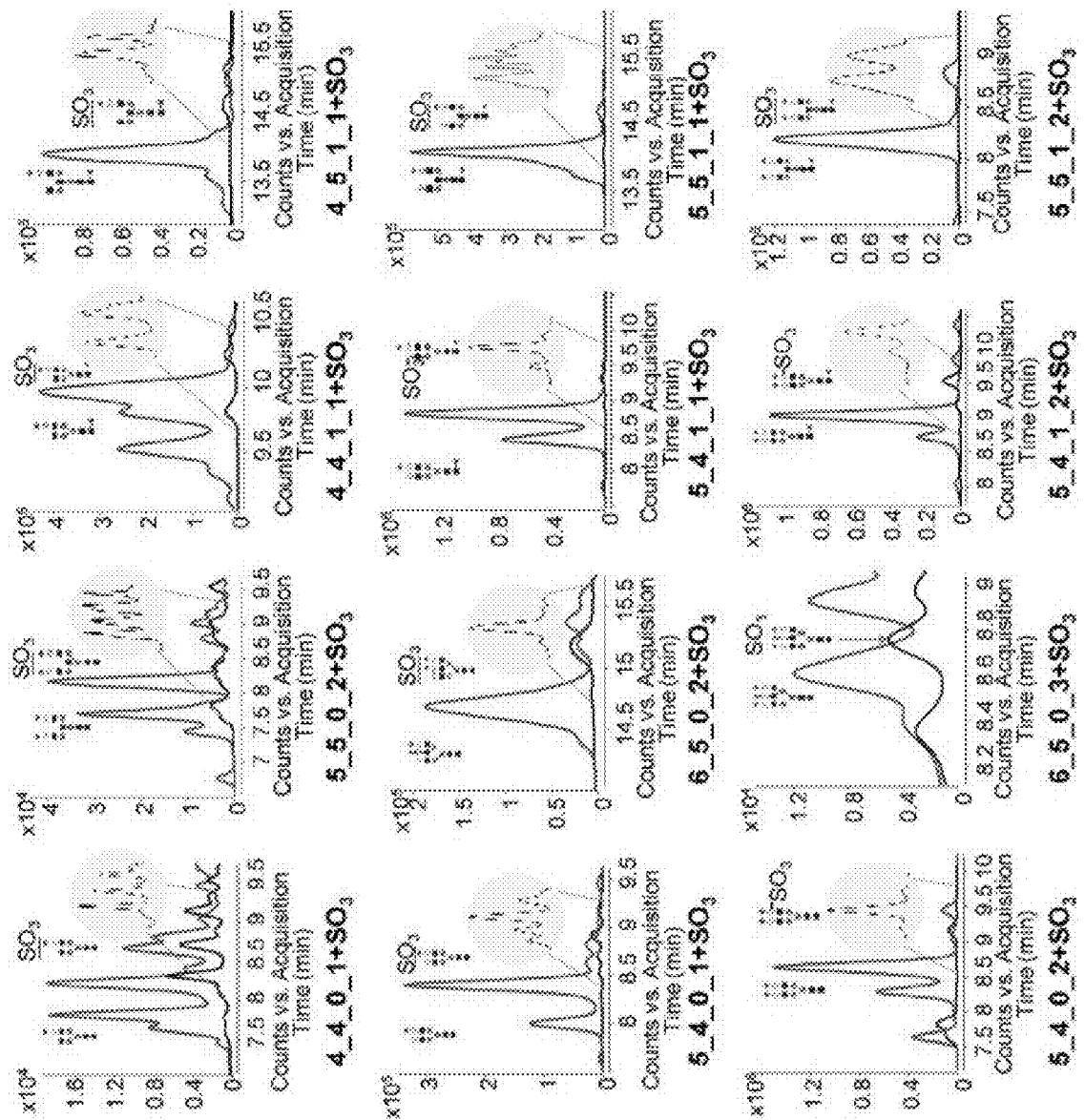
Figure 3E:
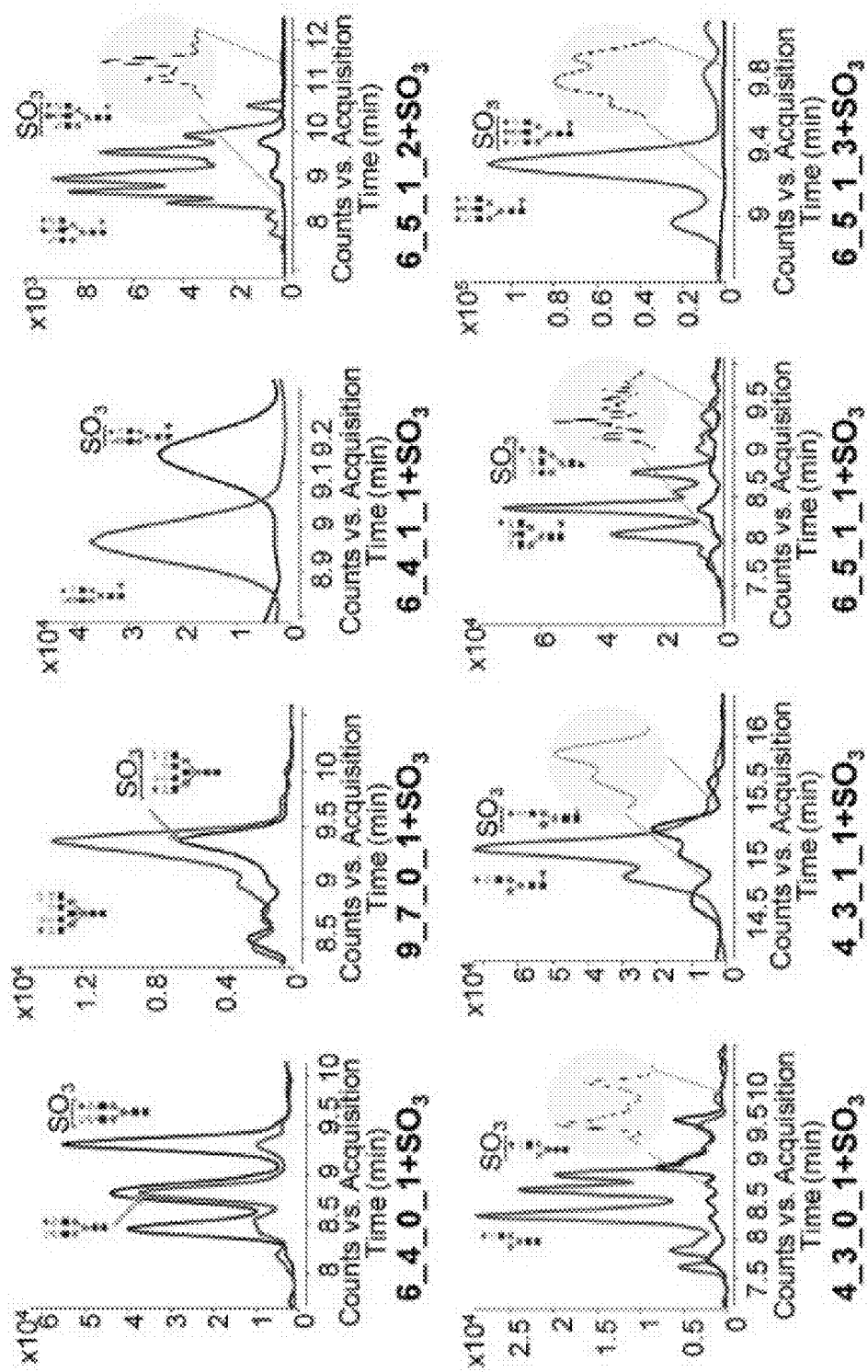

As illustrated in FIGS. 3D-3E, all sulfated N-glycans exhibited consistent retention time difference (typically +0.4 min) relative to their "parent" species (i.e. the retention time of each sulfated glycan is 0.4 min later than its corresponding parent glycan), and their signal intensities were 3- to 200-fold lower than those of non-sulfated counterparts. Sulfation constitutes a novel structural variation and represents another type of microheterogeneity expression of N-glycans on IgG.

Figures 4A, 4B:
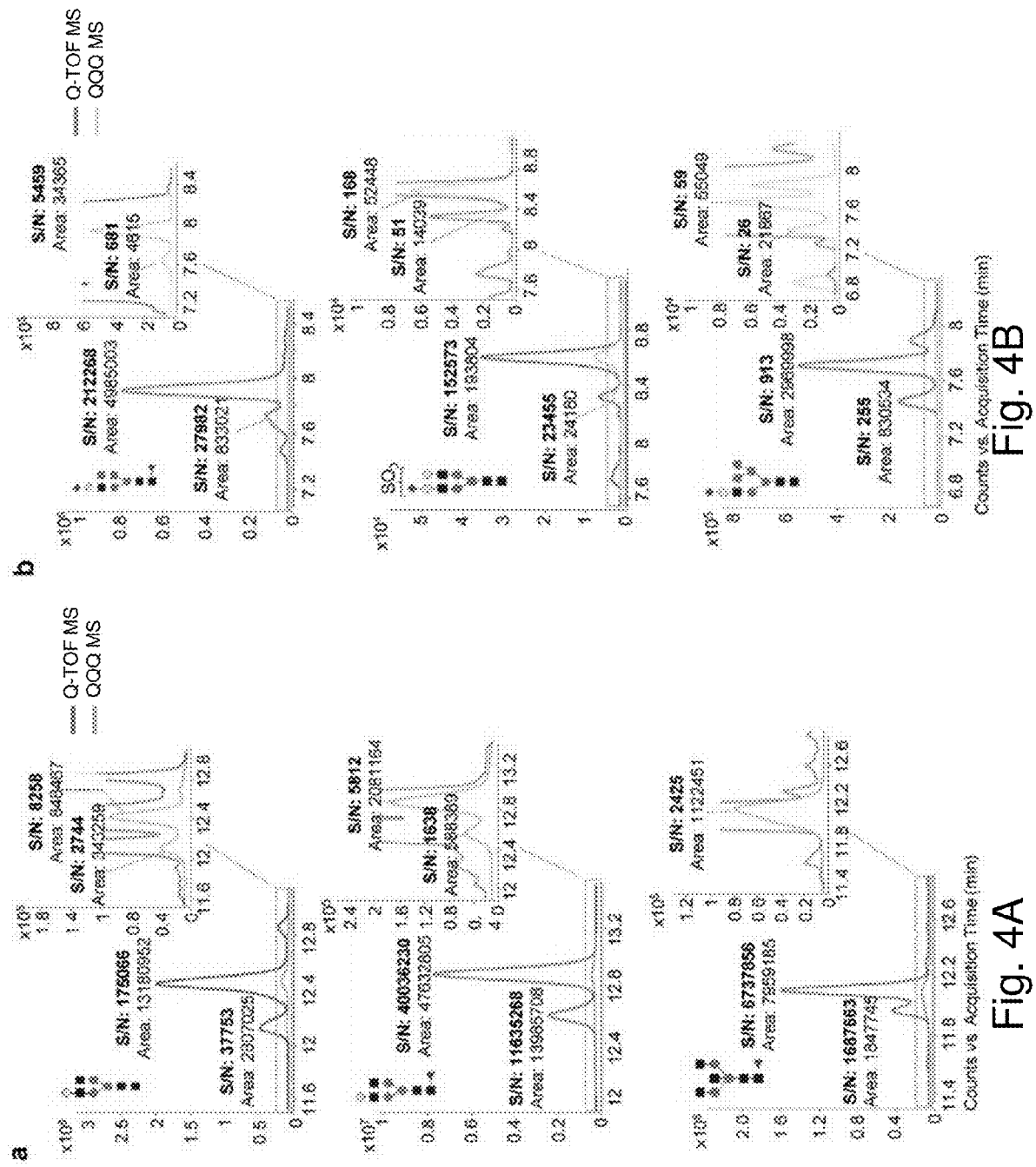
FIG. 4A, FIG. 4B, FIG. 4C and FIG. 4D show improved detection of N-glycans by using dynamic MRM method.

Multiple reaction monitoring (MRM) method was then used to quantify N-glycans of IgG, further improving the signal intensity of those low-abundance acidic N-glycans by about 1000-fold compared to that by TOF-MS, as shown in FIGS. 4A and 4B, in which N-glycans were detected by using Q-TOF MS (pale blue or pale red) and QqQ MS (MRM mode, blue or red), respectively. The improved detection for representative examples of neutral glycans, Hex$_4$HexNAc$_4$, Hex$_4$HexNAc$_4$dHex$_1$ and Hex$_3$HexNAc$_5$dHex$_1$, were shown in FIG. 4A, while the improved detection of representative sialylated glycans, Hex$_5$HexNAc$_3$dHex$_1$NeuAc$_1$, Hex$_5$HexNAc$_4$NeuAc$_1$+SO$_3$ and Hex$_6$HexNAc$_3$NeuAc$_1$, were shown in FIG. 4B. The SNR of the glycans obtained by MRM increased up to 1000-fold as compared to that obtained on TOF-MS.

Figure 4C:
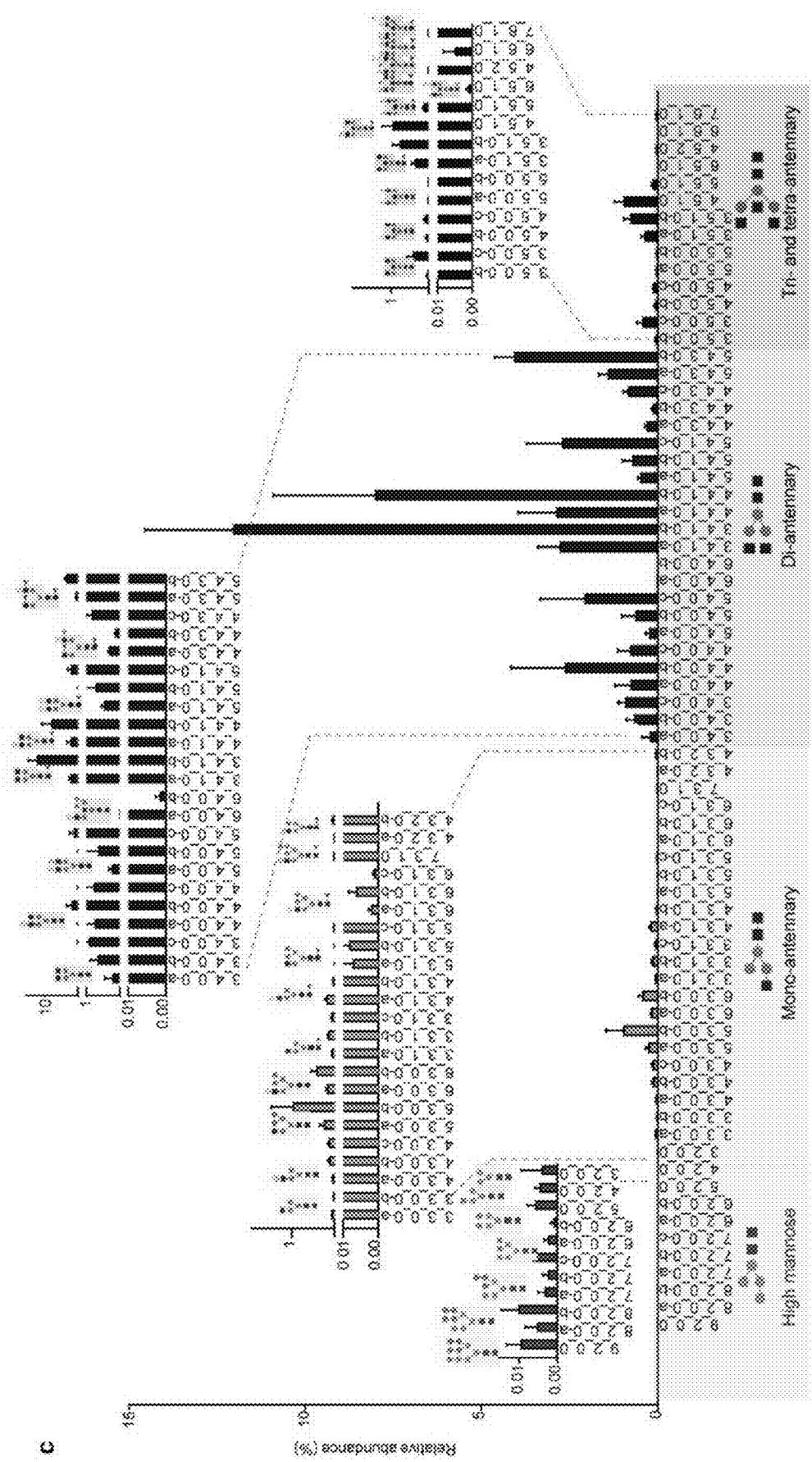
Figure 4D:
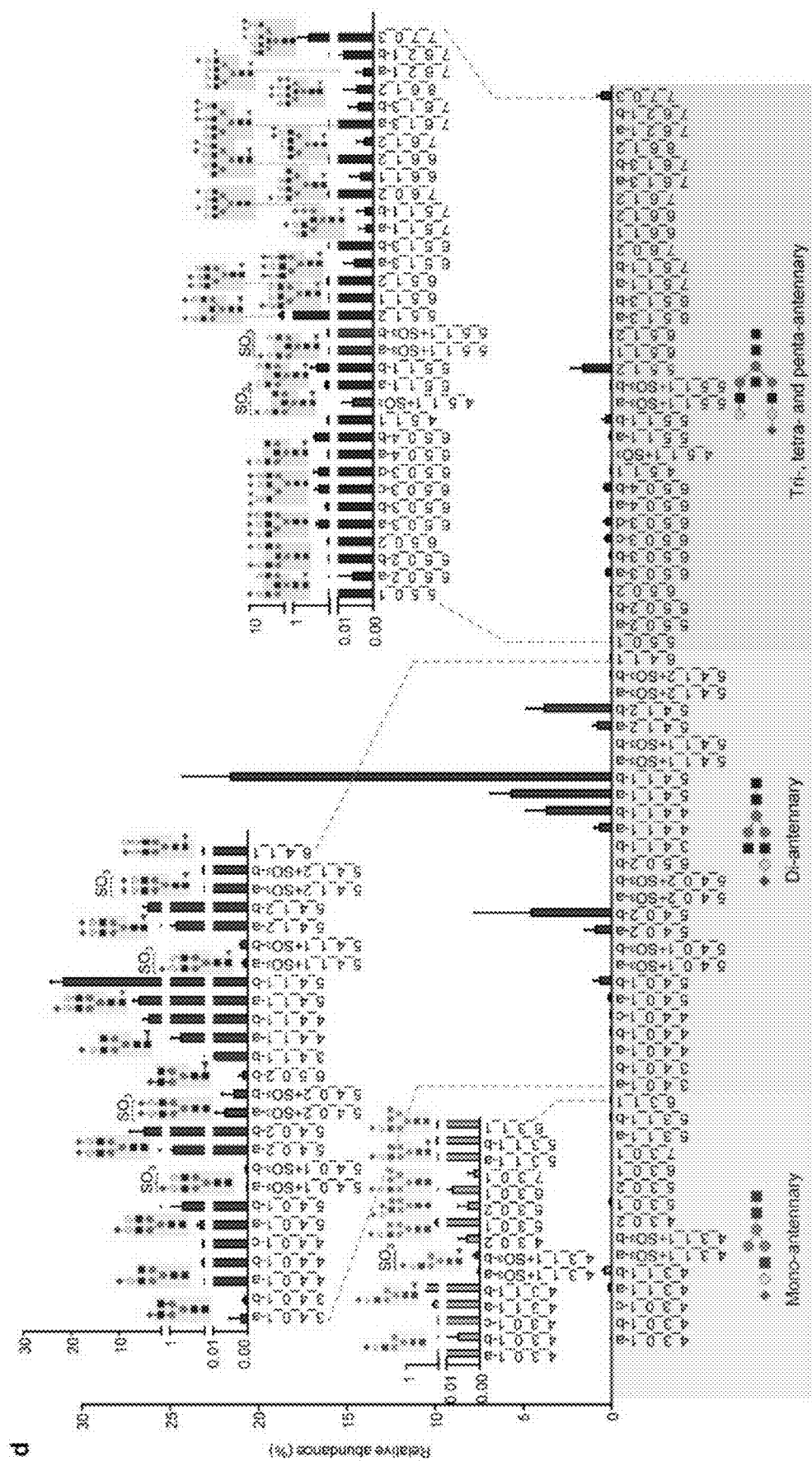

The lower limit of quantification (LLOQ) of acidic N-glycans was determined as 10- to 100-fold higher than that determined by TOF-MS. In particular, employment of TiO$_2$ enrichment enabled the highly sensitive detection of acidic glycans to mix with complex neutral glycans, owing to the removal of ionization suppression/interference derived from high-abundance neutral glycans. This quantitative method demonstrated a much wider linearity (typically 500- to 1000-fold) as compared to TOF-MS (generally 16- to 100-fold). With MRM method, the signal intensities of acidic glycans can be pointedly enhanced by increasing dwell time, thus significantly reducing "ionization bias". This MS/MS-based method was further validated for its recovery rate and selectivity. Quantitative glycomic profiling of human serum IgGs by using this approach revealed remarkable "depth" in the concentration of individual glycans, as shown in FIGS. 4C-4D, illustrating high dynamic range of up to 5 orders of magnitude in the relative abundance of both neutral glycans (as shown in FIG. 4C) and acidic glycans (as shown in FIG. 4D).

To explore the potential biological role of the acidic glycans, the inventors extended their analysis to serum samples from RA patients. The entire N-glycome of the serum IgG of 90 RA patients and 57 healthy subjects was quantitatively analyzed using MRM. To visualize the correlation of glycosylation changes with disease progress, the relative abundance of individual glycans was employed as variations to predict the grouping of subjects by using Support Vector Machine (SVM). As shown in FIGS. 5A to 5C, an overall trend of "the minor, the more widely changed" was observed for both neutral and acidic glycans. FIGS. 5A to 5C respectively showed relative abundance of 9 neutral glycans (bars in blue in FIG. 5A), 8 sialylated glycans (bars in red in FIG. 5B) and 4 sulfated glycans (bars in purple in FIG. 5C) on serum IgGs of healthy subjects (n=57) and RA patients (n=90).

Figure 5F:
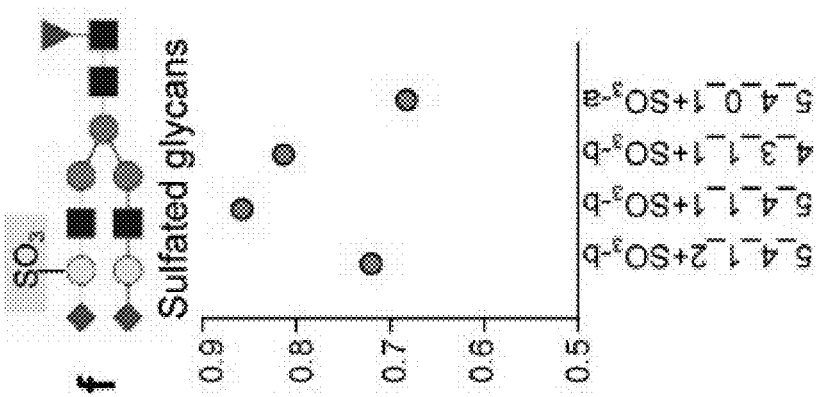
Figure 5E:
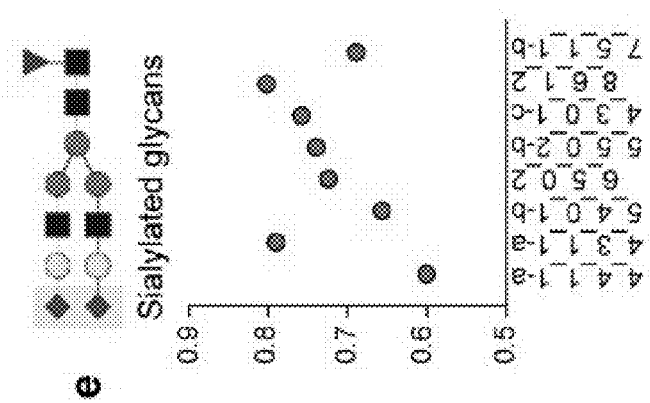
Figure 5D:
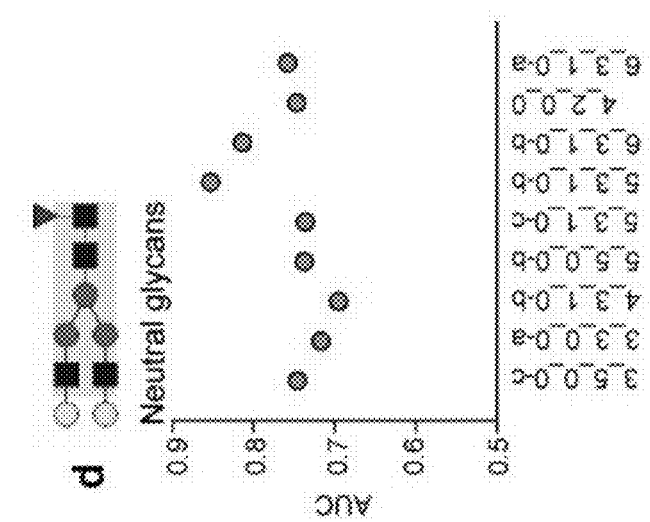
Figure 5H:
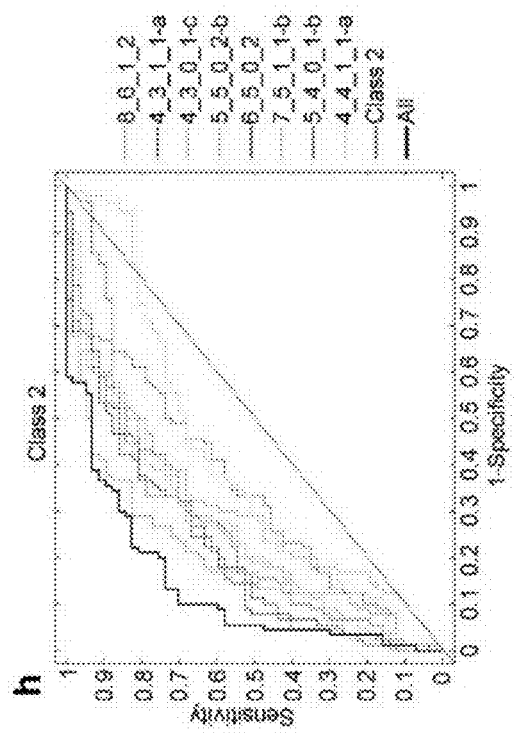
Figure 5I:
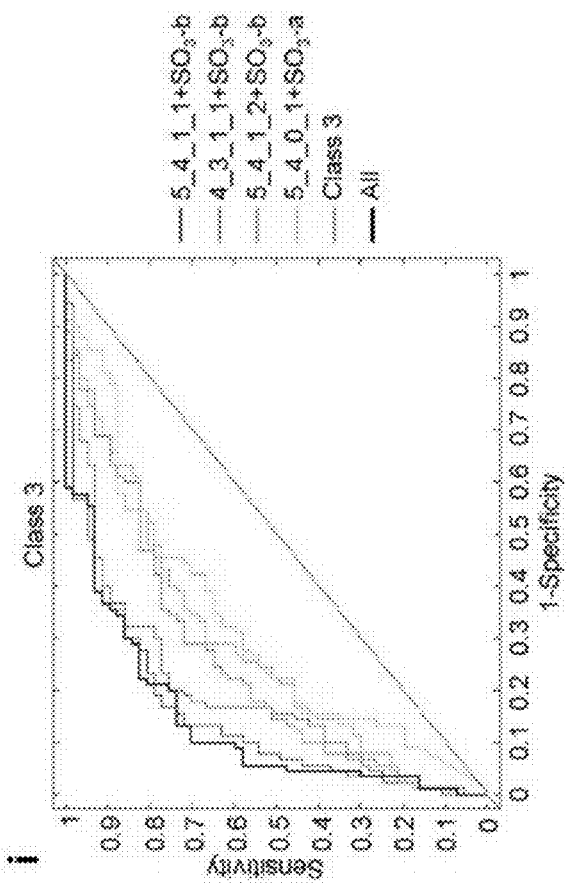
Figure 5G:
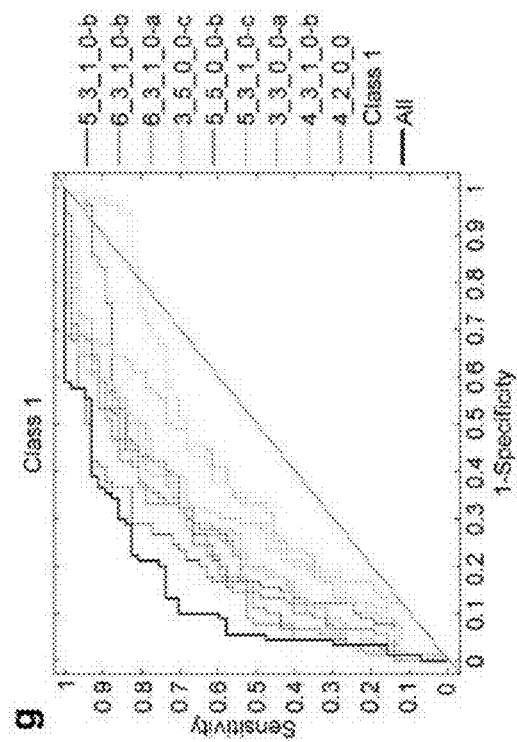
Figure 5J:
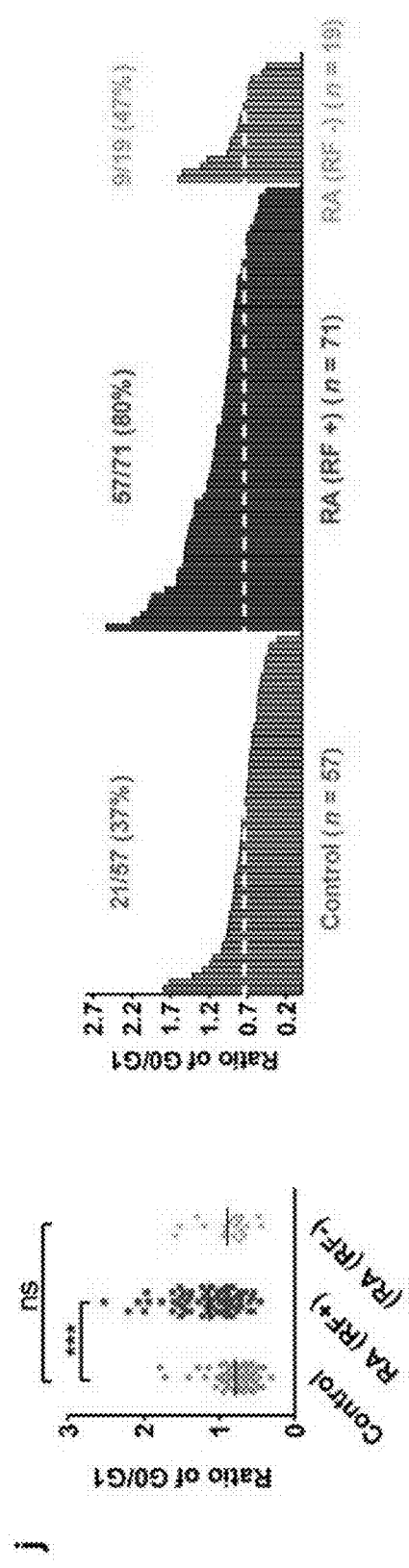
Figure 5K:
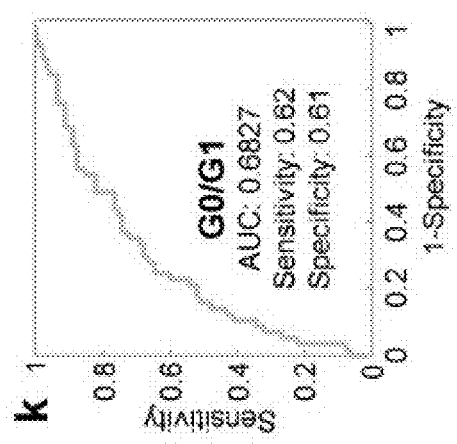

The Receiver Operator Characteristic (ROC) curves were further constructed for the glycans markers that were identified as being significantly changed in RA patients, as shown in FIGS. 5G to 5I. The glycan markers, as a whole, generated a sensitivity of 0.82 and specificity of 0.78, combined with an AUC (area under the curve) of 0.87. For individual potential glycans biomarkers, the AUC values for ROC analysis ranged from 0.60 to 0.86, as shown in FIGS. 5D-5F. Notably, as shown in FIG. 5F, a number of sulfated glycans were identified as markers for distinguishing RA patients from controls, among which 2 sulfated glycans, namely 4_3_1_1+SO$_3$-b (i.e. item 10 of FIG. 3A) and 5_4_1_1+SO$_3$-b (i.e. item 12 of FIG. 3A), yielded high AUCs (as shown in FIGS. 5C and 5I), indicating their potential values in the diagnosis of RA.

Figure 5L:
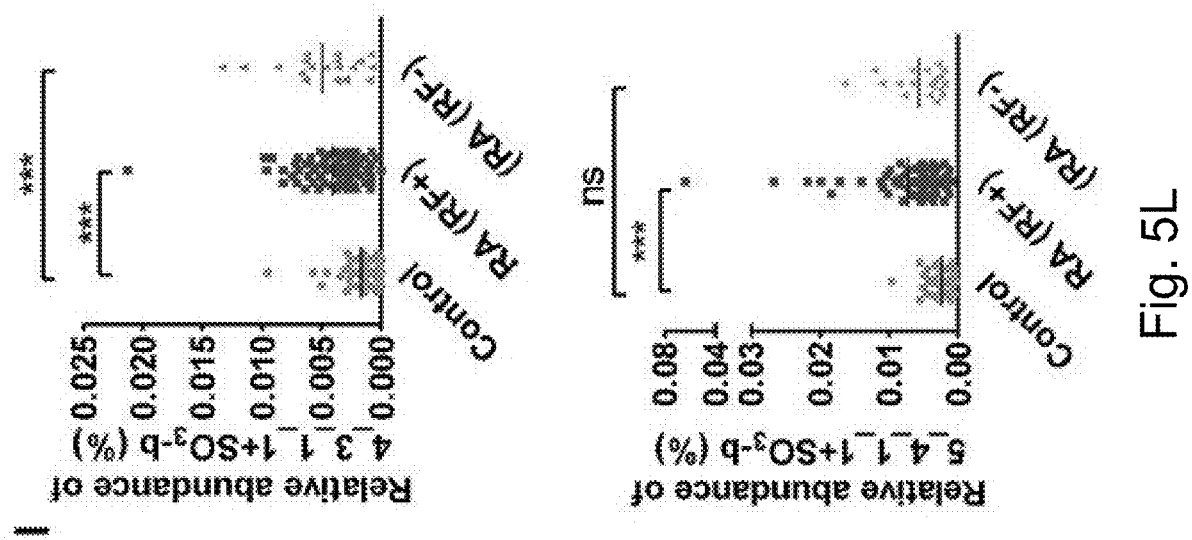
Figure 5M:
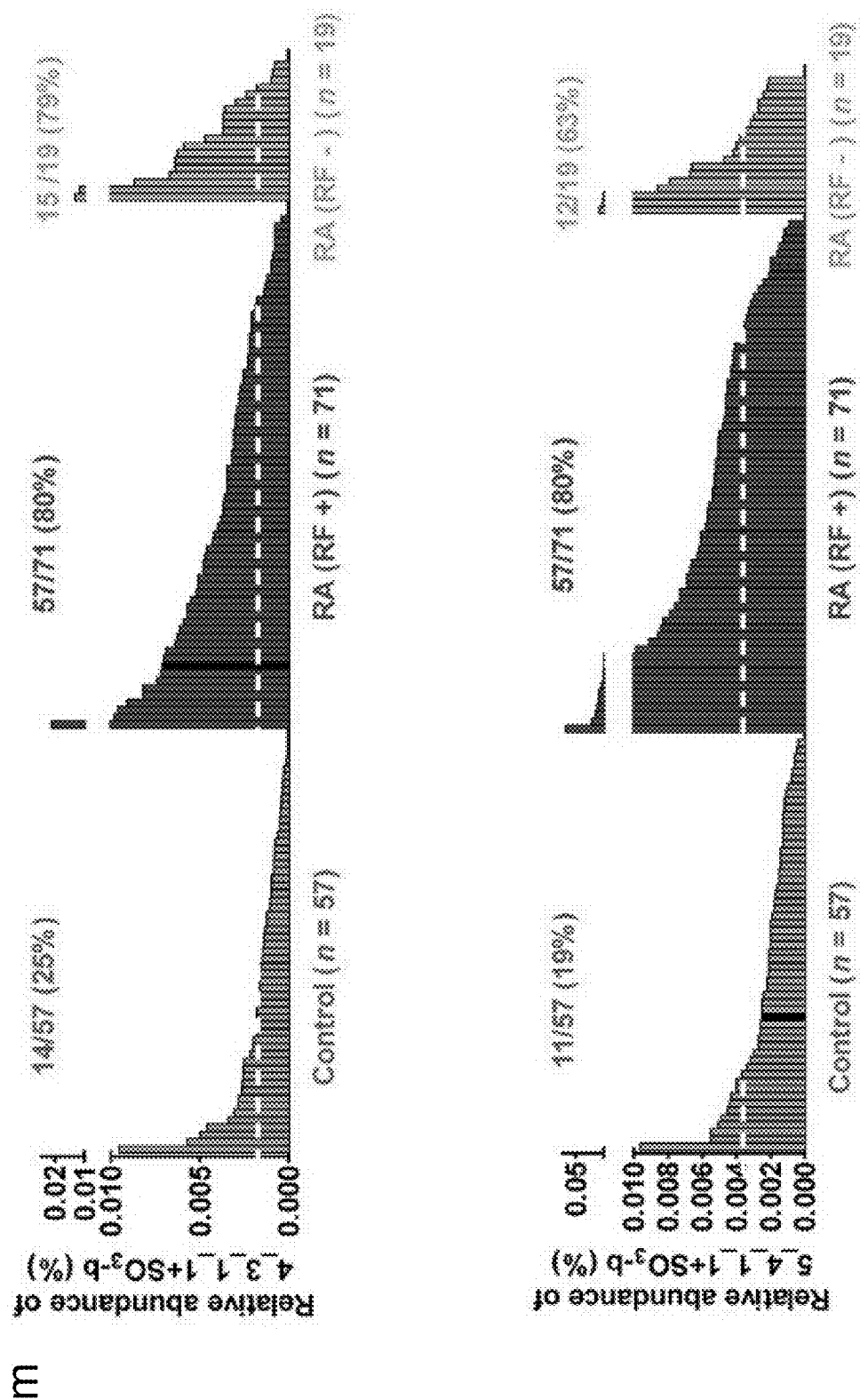
Figure 5N:
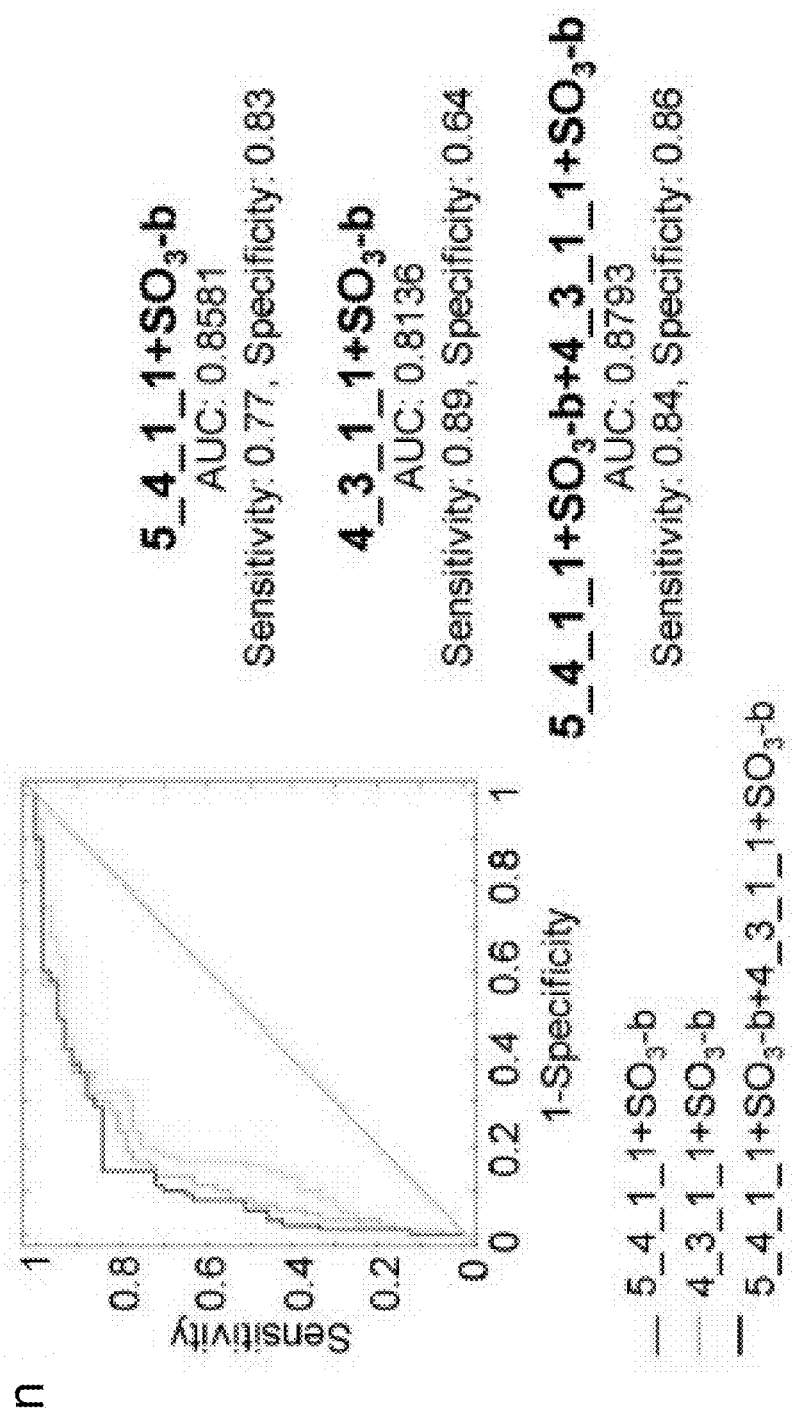

In particular, FIGS. 5G to 5I show ROC curve of neutral, sialylated and sulfated glycan markers respectively. FIGS. 5J to 5N show the potential of previously identified marker (G$_0$/G$_1$) and newly identified sulfated glycan markers, namely 5_4_1_1+SO$_3$-b (i.e. item 12 of FIG. 3A) and 4_3_1_1+SO$_3$-b (i.e. item 10 of FIG. 3A), to differentiate healthy subjects (n=57), RF-positive patients (n=71) and RF-negative patients (n=19). For each glycan marker, a scatter plot of the relative abundance in the healthy subjects (Control), RF-positive [RA (RF+)] RA patients and RF-negative [RA (RF−)] RA patients as shown in FIG. 5L. A column bar plot of each glycan marker in the control, RF-positive RA patients and RF-negative RA patients as shown in FIG. 5M, in which the dashed line (in white) indicated a threshold relative abundance that can differentiate 80% of the RF-positive RA patients. The ROC curves of the markers were given in the FIGS. 5K and 5N.

Unlike previously reported serum glycan markers, e.g., the ratio of G$_0$/G$_1$, the newly identified glycan markers, especially sulfated glycans, exhibited high potential for the classification of RF-negative RA patients, as shown in FIGS. 5J to 5N, with a combined accuracy reaching 94%. As RF-independent markers, they hold promise for the diagnosis of autoantibody-negative patients. In addition, as glycan makers of total IgG, rather than autoantibody-specific IgG, the on-chip method readily lends itself to clinical application.

Any changes in the structures or levels of even trace glycans could result in significant physiological/pathological events. By sharp increase in glycome coverage and depth, chip-based approach devised by the inventors provides an early glimpse into the remarkable structural complexity of N-glycans resulting from microheterogeneity expressions, such as sulfation and acetylation. Moreover, since all N-glycans share a common core sugar sequence, the TiO$_2$-PGC chip-based glycomic approach is obviously applicable for profiling N-glycans released from any single glycoprotein or total glycoproteins. N-glycosylation occurs on numerous secreted and membrane-bound glycoproteins, and glycan components are often the crucial functional determinants of biological events. Therefore, the glycomic approach of the inventors will rapidly position itself as one of the most important tools in addressing some key biological and pathological questions. Moreover, owing to the conserved biosynthesis of N-glycans across metazoa, plants, yeast and even bacteria, this on-chip glycomic approach could be further extrapolated to the area of vaccine design because antigen glycosylation, including N-glycosylation, has been increasingly appreciated as essential in adaptive immune activation, as well as the quality control of antibody-based drugs.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:

1. A microfluidic chip for enriching trace glycan from a mixture of glycans comprising an enrichment column that attaches to an analytical column,
   wherein said enrichment column enriches acidic glycans and includes
       a first section that includes porous graphitized carbon;
       a second section that connects to said first section and includes titanium dioxide; and
       a third section that connects to said second section and includes porous graphitized carbon;
   wherein said analytical column includes porous graphitized carbon;
   wherein said first section and said third section of said enrichment column perform pre-enrichment of glycans to remove non-glycan constituents; said second section of said enrichment column performs enrichment of acidic glycans; and said analytical column performs chromatographic separation of glycans, such that detection sensitivity of trace glycans is enhanced when a mixture of glycans runs through the microfluidic chip.

2. The microfluidic chip of claim 1 wherein said microfluidic chip has enhanced detection sensitivity of sulfated glycan.

3. The microfluidic chip of claim 1 wherein said microfluidic chip has enhanced detection sensitivity of sulfated glycan comprising a structure set forth in FIG. 3A.

4. A method of improving detection sensitivity of trace glycan from a mixture of glycans comprising:
   a) loading a sample of said mixture of glycans onto an enrichment column;
   b) running neutral glycans from step (a) onto an analytical column that performs chromatographic separation of glycans while acidic glycans are retained on said enrichment column and
   c) running the acidic glycans from step (b) onto the analytical column to achieve analysis of the acidic glycans;
   wherein said enrichment column enriches acidic glycans while said analytical column performs chromatographic separation of glycans,
   wherein said enrichment column comprises two porous graphitized carbon sections and one titanium dioxide section sandwiched between said two porous graphitized carbon sections.

5. The method of claim 4 wherein said analytical column comprises porous graphitized carbon.

6. The method of claim 4 wherein said trace glycan is acidic glycan.

7. The method of claim 4 wherein said trace glycan is sulfated glycan.

8. The method of claim 4 wherein said trace glycan comprises a structure set forth in FIG. 3A.

9. The method of claim 4 wherein the sample of said mixture of glycans is loaded onto the enrichment column using 0.6% acetic acid, 2% formic acid (FA) and 2% acetonitrile (ACN) in water at a flow rate of 3 mL/min.

10. The method of claim 4 wherein the neutral glycans are analyzed in the analytical column with a mobile phase consisting of:
    solution A comprising 1% FA in water; and
    solution B comprising ACN;
wherein the acidic glycans are analyzed in the analytical column with a different mobile phase consisting of:
    solution A' comprising 0.5% FA in water adjusted to pH3 by ammonia solution; and
    solution B' comprising 1% FA in ACN.

11. The method of claim 10 wherein the mobile phase for analyzing the neutral glycans is applied for 6 minutes with 95% of the solution A and 5% of the solution B, followed by 10 minutes with 40% to 95% of the solution A and 5% to 60% of the solution B, followed by 3 minutes with 20% of the solution A and 80% of the solution B.

12. The method of claim 10 wherein the mobile phase for analyzing the acidic glycans is applied for 1 minute with 95% of the solution A' and 5% of the solution B', followed by 10 minutes with 40% to 95% of the solution A' and 5% to 60% of the solution B', followed by 3 minutes with 20% of the solution A' and 80% of the solution B'.

13. The method of claim 4 wherein the acidic glycans retained on the enrichment column is eluted by injecting 5 μL of elution buffer comprising 0.5% ammonia solution in water.

* * * * *